United States Patent [19]
Breu et al.

[11] Patent Number: 6,004,965
[45] Date of Patent: Dec. 21, 1999

[54] SULFONAMIDES

[75] Inventors: Volker Breu, Schliengen, Germany; Kaspar Burri, Binningen, Switzerland; Jean-Marie Cassal, Mulhouse, France; Martine Clozel, St. Louis, France; Georges Hirth, Huningue, France; Bernd-Michael Löffler, Oberrimsingen, Germany; Marcel Müller, Frenkendorf, Sweden; Werner Neidhart, Hagenthal le Bas, France; Henri Ramuz, Birsfelden, Sweden

[73] Assignee: Hoffmann-La Roche Inc., Nutley, N.J.

[21] Appl. No.: 08/860,107

[22] PCT Filed: Dec. 8, 1995

[86] PCT No.: PCT/EP95/04843

§ 371 Date: Aug. 15, 1997

§ 102(e) Date: Aug. 15, 1997

[87] PCT Pub. No.: WO96/19459

PCT Pub. Date: Jun. 27, 1996

[30] Foreign Application Priority Data

Dec. 20, 1994 [CH] Switzerland .............................. 3837/94
Aug. 24, 1995 [CH] Switzerland .............................. 2419/95

[51] Int. Cl.[6] .................. A01N 43/54; C07D 413/00; C07D 401/00; C07D 403/00
[52] U.S. Cl. ............................. 514/256; 544/82; 544/238; 544/296
[58] Field of Search ............................. 514/256; 544/82, 544/296, 238

[56] References Cited

U.S. PATENT DOCUMENTS

| | | | |
|---|---|---|---|
| 5,270,313 | 12/1993 | Burri et al. | 514/252 |
| 5,292,740 | 3/1994 | Burri et al. | 514/256 |
| 5,420,129 | 5/1995 | Breu et al. | 514/252 |

FOREIGN PATENT DOCUMENTS

| | | |
|---|---|---|
| 2125730 | 12/1994 | Canada . |
| 0510526 | 10/1992 | European Pat. Off. . |
| 0526708 | 2/1993 | European Pat. Off. . |
| 0633259 | 1/1995 | European Pat. Off. . |
| 0658548 | 6/1995 | European Pat. Off. . |

*Primary Examiner*—Mukund J. Shah
*Assistant Examiner*—Tamthom N. Truong
*Attorney, Agent, or Firm*—George W. Johnston; William H. Epstein; John P. Parise

[57] ABSTRACT

Compounds of the formula:

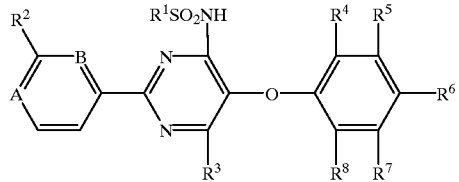

where A, B, $R^1$–$R^8$ are as described herein are endothelin inhibitors that can be used in treating diseases associated with endothelin, such as high blood pressure. Chemical synthesis of these compounds and pharmaceutical compositions containing these compounds are also useful.

86 Claims, No Drawings

SULFONAMIDES

This patent application is filed pursuant to 35 U.S.C. §371 based on PCT/EP95/04843, filed Dec. 8, 1995.

The present invention is concerned with novel sulphonamides and their use as medicaments. In particular, the invention is concerned with novel compounds of the formula

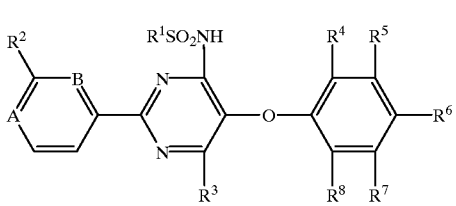

wherein
$R^1$ signifies phenyl or phenyl substituted by halogen, $C_{1-7}$-alkyl, $C_{1-7}$-alkoxy, $C_{1-7}$-alkylenedioxy, carboxyl or trifluoromethyl; or heterocyclyl selected from mono- or bicyclic, 5- and 6-membered heterocycles having oxygen, nitrogen or sulphur as the hetero atom;
$R^2$ signifies tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino or hydroxyamidino;
$R^3$ signifies a residue $-O-(CR^aR^b)_n-OR^9$;
$R^4-R^8$ signify hydrogen, $C_{1-7}$-alkoxy or halogen;
$R^9$ signifies hydrogen, benzyl, benzyl substituted in the phenyl ring by halogen, $C_{1-7}$-alkyl, $C_{1-7}$-alkoxy, $C_{1-7}$-alkylenedioxy, carboxyl or trifluoromethyl; or a residue $-C(O)NHR^{10}$;
$R^{10}$ signifies $C_{1-7}$-alkyl, phenyl, phenyl substituted by halogen, $C_{1-7}$-alkyl, $C_{1-7}$-alkoxy, $C_{1-7}$-alkylenedioxy, carboxyl or trifluoromethyl; or pyridyl or pyridyl substituted by 1 or 2 $C_{1-7}$-alkyl groups;
$R^a$ and $R^b$ signify hydrogen or $C_{1-7}$-alkyl;
n signifies 2, 3 or 4; and
A and B signify CH; or one of the symbols A or B signifies nitrogen and the other signifies CH; or
$R^2$ signifies hydrogen and one of the symbols A or B signifies N-oxide (N→O) and the other signifies CH,
and pharmaceutically usable salts of compounds of formula I.

Examples of residues of mono- or bicyclic, 5- and 6-membered heterocycles having oxygen, nitrogen or sulphur as the hetero atom, such as 2- and 3-furyl, 2-, 4- and 5-pyrimidinyl, 2-, 3- and 4-pyridyl, 1,2- and 1,4-diazinyl, 2- and 3-thienyl, oxazolyl, thiazolyl, imidazolyl, benzofuranyl, benzothienyl, purinyl, quinolyl, isoquinolyl and quinazolyl, which residues can be substituted, e.g. by 1 or 2 $C_{1-7}$-alkyl groups. Preferred are pyridyl or pyridyl substituted by 1 or 2 $C_{1-7}$-alkyl groups.

The term "$C_{1-7}$" used here denotes groups with 1–7 C atoms, preferably 1–4 C atoms. Alkyl and alkoxy groups can be straight-chain or branched. Methyl, ethyl, propyl, isopropyl, butyl, sec. and tert.butyl are examples of such alkyl groups. Halogen denotes fluorine, chlorine, bromine and iodine, with chlorine being preferred.

A preferred group of compounds of formula I comprises those in which A and B are CH or one of the symbols A and B is nitrogen. $R^1$ is preferably a phenyl residue, which is mono- or di-substituted, or a pyridyl residue, which is mono-substituted by $C_{1-7}$-alkyl, especially an $C_{1-7}$-alkyl substituted 2-pyridyl residue. $R^2$ is preferably a tetrazolyl residue. $R^3$ is preferably $-O(CH_2)_nOH$, $-O(CH_2)_nO$-benzyl or $-O(CH_2)_nOC(O)NHR^{10}$, in which $R^{10}$ is pyridyl, especially 2-pyridyl. n is preferably 2. Of particular interest among these compounds are those in which $R^4$ is $C_{1-7}$-alkoxy and $R^5-R^8$ are hydrogen; or $R^4$ is halogen, $R^7$ is $C_{1-7}$-alkoxy and $R^5$, $R^6$ and $R^8$ are hydrogen; A is nitrogen and B is CH.

The documents, EP-A-0 510 526 and EP-A-0 526 708 disclose sulfonamides having endothelin-inhibiting activity.

The compounds of formula I can be manufactured by
a) reacting a compound of formula II

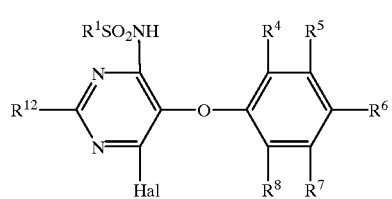

wherein $R^{12}$ is 3- or 4-cyanophenyl or 2- or 4-pyridyl N-oxide and Hal is halogen and the remaining symbols have the significance set forth above,
with a compound of the formula $MO-(CR^aR^b)_n-OR^{91}$, wherein M is an alkali metal and $R^{91}$ is hydrogen, benzyl or benzyl substituted in the phenyl ring by halogen, $C_{1-7}$-alkyl, $C_{1-7}$-alkoxy, $C_{1-7}$-alkylenedioxy, carboxyl or trifluoromethyl; and $R^a$, $R^b$ and n have the significance set forth above;
or
b) reacting a compound of formula III

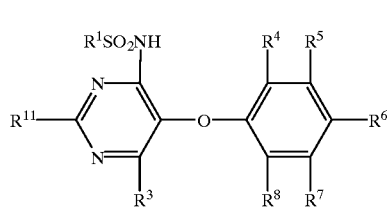

wherein $R^{11}$ is 2- or 4-pyridyl N-oxide and the remaining symbols have the significance set forth above,
with a trialkylsilyl cyanide and a trialkylamine; or
c) reacting a compound of formula I in which $R^2$ is cyano and the remaining symbols have the significance set forth above with an azide in the presence of an aprotic Lewis acid; or
d) converting a compound of formula I in which $R^2$ is cyano and the remaining symbols have the significance set forth above with an alkali metal alcoholate and thereafter with hydrazine into the corresponding amidrazone and treating this with a nitrite and an acid; or
e) reacting a compound of formula I in which $R^9$ is hydrogen with an isocyanate of the formula $R^{10}NCO$; or
f) transforming the cyano group in a compound of formula I in which $R^2$ is cyano and the remaining symbols have the significance set forth above into an amidino, carbamoyl, thiocarbamoyl, $C_{1-7}$-alkoxycarbonyl, carboxy, hydroxymethyl, formyl or hydroxyamidino group; or
g) alkylating the tetrazolyl group in a compound of formula I in which $R^2$ is tetrazolyl and $R^9$ is benzyl, benzyl substituted in the phenyl ring by halogen, $C_{1-7}$-alkyl, $C_{1-7}$-alkoxy, $C_{1-7}$-alkylenedioxy, carboxyl or trifluoromethyl; and cleaving off a hydroxy protecting group from the reaction product;
and, if desired, converting a compound of formula I obtained into a salt.

The reaction of a compound of formula II with a compound of the formula $MO(CR^aR^b)_nOR^{91}$ (process variant a) is conveniently carried out in a glycol corresponding to this compound as the solvent, e.g. in ethylene glycol when n=2 and $R^a$ and $R^b$ are hydrogen. The alkali metal M is preferably sodium and Hal is preferably chlorine. The reaction is conveniently carried out while heating, e.g. to 40–100° C. According to this process variant there are obtained compounds of formula I in which $R^2$ signifies cyano and A and B signify CH; or $R^2$ signifies hydrogen and one of the symbols A or B signifies N-oxide and the other signifies CH, and $R^9$ is a residue $R^{91}$ as defined above, and the remaining symbols have the given significance.

In process variant b) a N-oxide of formula II is preferably reacted with trimethylsilyl cyanide and triethylamine. The reaction is conveniently carried out in acetonitrile while heating to the reflux temperature of the reaction mixture. According to this process variant there are obtained compounds of formula I in which $R^2$ signifies cyano and one of the symbols A or B signifies nitrogen and the other signifies CH and the remaining symbols have the given significance.

In the reaction according to process variant c) there can be used as the azide e.g. sodium azide, guanidinium azide or trimethylsilyl azide. Ammonium salts, e.g. ammonium chloride, can be used as Lewis acids. The reaction can be carried out in an aprotic, polar solvent such as dimethylformamide or dimethyl sulphoxide, conveniently while heating, e.g. to a temperature of 60–100° C.

The reaction of a compound of formula I in which $R^2$ is cyano with hydrazine according to process variant d) proceeds via the iminoether, from which the amidrazone, i.e. a compound corresponding to formula I with $R^2$=—CH(NH)NHNH$_2$, is obtained with excess hydrazine. The amidrazone is converted by nitrosation into an iminoazide which cyclizes spontaneously to the tetrazole. According to process variants c) and d) there are obtained compounds of formula I in which $R^2$ signifies tetrazolyl and the remaining symbols have the given significance.

The reaction in accordance with process variant e) can be effected in a manner known per se for the preparation of carbamates from alcohols and isocyanates, e.g. in in a suitable anhydrous organic solvent, e.g. a hydrocarbon such as toluene, conveniently while heating. The isocyanate can be generated in situ, e.g. from an azide of the formula $R^{10}CON_3$ by thermal rearrangement. According to this process variant there are obtained compounds of formula I in which $R^9$ signifies a residue —C(O)NHR$^{10}$ and the remaining symbols have the given significance.

The transformation of a cyano group $R^2$ in a compound of formula I into an amidino, carbamoyl, thiocarbamoyl, lower-alkoxycarbonyl, carboxy, hydroxymethyl, formyl or hydroxyamidino group in accordance with process variant f) can be effected in a manner known per se for such transformations. For example, the cyano group can be converted by treatment with alkali alcoholate, e.g. with sodium methylate in methanol, into an iminoether (i.e., the group C(NH)OCH$_3$) which can be converted in situ by treatment with hydrochloric acid into an alkyl carboxylate (e.g. the group —COOCH$_3$), which can be saponified to the carboxylic acid by treatment with alcoholic alkali. Alternatively, the iminoether, obtained in situ, can be transformed by treatment with ammonium chloride in methanol into the corresponding amidino compound ($R^2$=amidino) and this can be transformed by treatment with aqueous alkali and subsequent acidification into the corresponding carbamoyl compound ($R^2$=—C(O)NH$_2$)). By treatment of the iminoether, obtained in situ, with hydroxylamine and aqueous sodium acetate solution there can be obtained the corresponding hydroxyamidino compounds ($R^2$=—C(NH)NHOH). A carboxy group can be reduced by treatment with reducing agents such as sodium dihydro-bis-(2-methoxyethoxy) aluminate in toluene to the hydroxymethyl group and this can be oxidized to the formyl group by treatment with oxidizing agents such as manganese dioxide. In these reaction sequences $R^3$ should not contain a hydroxy group, i.e. $R^9$ should not represent hydrogen, but should represent e.g. benzyl.

The alkylation of a compound of formula I in accordance with process variant g) can be carried out in a manner known per se, e.g. by treatment with a lower-alkyl halide in the presence of a base such as K tert.-butylate in tetrahydrofuran, whereby a thus-obtained mixture of 1 - and 2-lower-alkyl-tetrazolyl compounds of formula I can be separated in a manner known per se, e.g. by chromatography. Suitable hydroxy protecting groups are e.g. alkylsilyl protecting groups such as dimethyl-tert.-butylsilyl and tetrahydropyranyl, which can be introduced and cleaved off from the reaction product in a manner known per se. According to process variant g) there are accordingly obtained compounds of formula I in which $R^2$ represents a lower-alkyl-tetrazolyl residue and $R^9$ represents hydrogen.

The compounds of formula I which contain a carboxy or tetrazolyl group can be converted in a manner known per se into pharmaceutically usable salts, e.g. alkali salts such as Na and K salts or alkaline earth metal salts such as Ca or Mg salts or salts with amines such as monoethanolamine.

The compounds which are used as starting materials, insofar as they are not known or their preparation is described hereinafter, can be prepared in analogy to known methods or to methods described below.

The compounds of formula I given above are endothelin receptor inhibitors. They can therefore be used for the treatment of disorders which are associated with endothelin activities, especially circulatory disorders such as hypertension, ischaemia, vasospasms and angina pectoris.

The inhibitory activity of the compounds of formula I on endothelin receptors can be demonstrated using the test procedures described hereinafter:
I: Inhibition of endothelin binding to recombinant ET$_A$ receptors A cDNA coding for human ET$_A$ receptors of human placenta was cloned (M. Adachi, Y. -Y. Yang, Y. Furuichi and C. Miyamoto, BBRC 180, 1265–1272) and expressed in the baculovirus-insect cell system. Baculovirus-infected insect cells from a 23 l fermenter are centrifuged off (3000×g, 15 minutes, 4° C.) 60 hours after the infection, re-suspended in Tris buffer (5 mM, pH 7.4, 1 mM MgCl$_2$) and again centrifuged. After a further re-suspension and centrifugation the cells are suspended in 800 ml of the same buffer and freeze-dried at −120° C. The cells disintegrate when the suspension in this hypotonic buffer mixture is thawed. After a repeated freeze-drying/thawing cycle the suspension is homogenized and centrifuged (25000×g, 15 minutes, 4° C.). After suspension in Tris buffer (75 mM, pH 7.4, 25 mM MgCl$_2$, 250 mM sucrose) 1 ml aliquots (protein content about 3.5 mg/ml) are stored at −85° C.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM MnCl$_2$, 1 mM EDTA and 0.5% bovine serum albumin). 100 μl of this membrane suspension containing 70 μg of protein are incubated with 50 μl of $^{125}$I-endothelin (specific activity 2200 Ci/mMol) in assay buffer (25000 cpm, final concentration 20 pM) and 100 μl of assay buffer containing varying concentrations of test compound. The incubation is carried out at 20° C. for 2 hours or at 4° C. for 24 hours. The separation of free and membrane-bound radio-ligands is carried out by filtration over a glass fibre filter. The inhibitory activity of compounds of formula I determined in this test procedure is given in Table 1 as the $IC_{50}$, i.e. as the concentration [nM] which is required to inhibit 50% of the specific binding of $^{125}$I-endothelin.

TABLE 1

| Compound of Example | $IC_{50}$ [nM] |
|---|---|
| 4 | 6 |
| 29 | 4 |
| 35 | 2 |
| 36 | 8 |
| 40 | 8 |
| 41 | 1 |

II. Inhibition of endothelin-induced contractions in isolated rat aorta rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% $O_2$ and 5% $CO_2$. The isometric stretching of the rings was measured. The rings were stretched to a pre-tension of 3 g. After incubation for 10 minutes with the test compound or vehicle cumulative dosages of endothelin-1 were added. The activity of the test compound was ascertained by the observed shift to the right of the dosage-activity curve of endothelin-1 in the presence of different concentrations of antagonist. This shift to the right (or "dose ratio", DR) corresponds to the quotient from the $EC_{50}$ values of endothelin-1 in the presence and in the absence of antagonist, with the $EC_{50}$ value denoting the endothelin concentration required for a half-maximum contraction.

The corresponding $pA_2$ value, which is a measure of the activity of the test compound, was calculated using a computer programme according to the following equation from the "dose ratio" DR for each individual dosage-activity curve.

$pA_2$=log(DR-1)-log(antagonist-concentration)

The $EC_{50}$ of endothelin in the absence of test compounds is 0.3 nM.

The $pA_2$ values obtained with compounds of formula I are given in Table 2.

TABLE 2

| Compound of Example | Dose ratio (switch to the right) |
|---|---|
| 4 | 9.60 |
| 29 | 10.0 |
| 35 | 9.5 |
| 36 | 9.4 |
| 40 | 10.2 |
| 41 | 10.6 |

On the basis of their capability of inhibiting endothelin binding, the compounds of formula I can be used as medicaments for the treatment of disorders which are associated with vasoconstriction of increasing frequencies. Examples of such disorders are high blood pressure, coronary disorders, cardiac insufficiency, renal and myocardial ischaemia, renal insufficiency, dialysis, cerebral ischaemia, cerebral infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The compounds of formula I can be administered orally, rectally, parentally, e.g. intravenously, intramuscularly, subcutaneously, intrathecally or transdermally; or sublingually or as opththalmological preparations, or as an areosol. Capsules, tablets, suspensions or solutions for oral administration, suppositories, injection solutions, eye drops, salves or spray solutions are examples of administration forms.

Intravenous, intramuscular or oral administration is a preferred form of use. The dosages in which the compounds of formula I are administered in effective amounts depend on the nature of the specific active ingredient, the age and the requirements of the patient and the mode of administration. In general, dosages of about 0.1–100 mg/kg body weight per day come into consideration. The preparations containing the compounds of formula I can contain inert or also pharmacodynamically active additives. Tablets or granulates e.g. can contain a series of binders, fillers, carriers or diluents. Liquid preparations can be present, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, e.g. water, gelatine, lactose, starch, magnesium stearate, talc, gum arabic, polyalkylene glycols and the like. It is a prerequisite that all adjuvants used in the manufacture of the preparations are non-toxic.

The following Examples illustrate the invention in more detail. DMF denotes dimethylformamide, THF denotes tetrahydrofuran and EtOAc denotes ethyl acetate.

EXAMPLE 1 a) 200 ml of dimethoxyethane and 110.9 g of 4-[4-(4-tert-butyl-phenyl-sulphonylamino)-6-chloro-5-(2-methoxy-phenoxy)-pyrimidin-2-yl]-pyridine 1-oxide are added all at once to a solution of 23.80 g of sodium in 660 ml of ethylene glycol. The solution is heated at 90° C. for 20 hours while stirring, thereafter cooled, poured into 2500 ml of $H_2O$ and thereafter treated with $CH_3COOH$ to pH 5. The mixture is extracted three times with EtOAc, the organic phase is washed with $H_2O$, dried with $Na_2SO_4$ and evaporated under reduced pressure. The residue is recrystallized from $CH_3CN$ and thereafter twice from a mixture of acetone and $CH_3CN$. There is thus obtained 4-[4-(4-tert-butyl-phenylsulphonylamino)-6-(2-hydroxy-ethoxy)-5-(2-methoxy-phenoxy)-pyrimidin-2-yl]-pyridine 1-oxide.

Preparation of the starting material:

b) 53.1 g of 4-cyano-pyridine (98%) are added all at once to a solution of 1.15 g of sodium in 200 ml of abs. MeOH. After 6 hours 29.5 g of $NH_4Cl$ are added while stirring vigorously. The mixture is stirred at room temperature overnight. 600 ml of ether are added thereto, whereupon the precipitate is filtered off under suction and thereafter dried at 50° C. under reduced pressure. There is thus obtained 4-amidino-pyridine hydrochloride (decomposition point 245–247° C.).

c) 112.9 g of diethyl (2-methoxyphenoxy)malonate are added dropwise within 30 minutes to a solution of 27.60 g of sodium in 400 ml of MeOH. Thereafter, 74.86 g of the amidine hydrochloride obtained in b) are added all at once. The mixture is stirred at room temperature overnight and evaporated at 50° C. under reduced pressure. The residue is treated with 500 ml of ether and filtered off under suction. The filter cake is dissolved in 1000 ml of $H_2O$ and treated little by little with 50 ml of $CH_3COOH$. The precipitate is filtered off under suction, washed with 400 ml of $H_2O$ and dried at 80° C. under reduced pressure. There is thus obtained 5-(2-methoxy-phenoxy)-2-(pyridin-4-yl)-pyrimidine-4,6-diol (or tautomer), melting point above 250° C.

d) A suspension of 154.6 g of 5-(2-methoxy-phenoxy)-2-(pyridin-4-yl)-pyrimidine-4,6-diol (or tautomer) in 280 ml of $POCl_3$ is heated at 120° C. in an oil bath for 24 hours while stirring vigorously. The reaction mixture changes gradually into a dark brown liquid which is evaporated under reduced pressure and thereafter taken up three times with 500 ml of toluene and evaporated. The residue is dissolved in 1000 ml of $CH_2Cl_2$, treated with ice and $H_2O$ and thereafter adjusted with 3N NaOH until the aqueous phase has pH 8. The organic phase is separated and the aqueous phase is extracted twice with $CH_2Cl_2$. The combined $CH_2Cl_2$ extracts are dried with $MgSO_4$, evaporated to half of the volume, treated with 1000 ml of acetone and the $CH_2Cl_2$ remaining is distilled off at normal pressure. After standing in a refrigerator for 2 hours the crystals are filtered off under suction and dried at 50° C. overnight. There is thus obtained 4,6-dichloro-5-(2-methoxy-phenoxy)-2-pyridin-4-yl)-pyrimidine, melting point 178–180° C.

e) A solution of 17.4 g of 4,6-dichloro-5-(2-methoxyphenoxy)-2-pyridin-4-yl)-pyrimidine in 100 ml of $CH_3CN$ is boiled at reflux for 3 hours with 15 ml of a 32% peracetic acid solution, thereafter cooled and stored in a refrigerator overnight. The crystals are filtered off under suction and dried at 50° C. under reduced pressure. There is thus obtained 4-[4,6-dichloro-5-(2-methoxy-phenoxy)-pyrimidin-2-yl]-pyridine 1-oxide, melting point 189–190° C.

f) A solution of 36.4 g of 4-[4,6-dichloro-5-(2-methoxy-phenoxy)-pyrimidin-2-yl]-pyridine 1-oxide and 52.8 g of p-tert-butylphenyl-sulphonamide potassium in 150 ml of abs. DMF is stirred at room temperature for 24 hours. Thereafter, it is poured into a mixture of 1500 ml of $H_2O$ and 1000 ml of ether while stirring mechanically, whereby a precipitate forms. The suspension is adjusted to pH 5 with $CH_3COOH$, suction filtered, the crystals are washed with cold water and thereafter with ether and dried at 50° C. There is thus obtained 4-[4-(4-tert-butyl-phenylsulphonylamino)-6-chloro-5-(2-methoxy-phenoxy)-pyrimidin-2-yl]-pyridine 1-oxide as a colourless material of melting point 247–249° C.

EXAMPLE 2

A solution of 78.45 g of 4-[4-(4-tert-butyl-phenylsulphonylamino)-6-(2-hydroxy-ethoxy)-5-(2-methoxy-phenoxy)-pyrimidin-2-yl]-pyridine 1-oxide, 122.5 g of trimethylsilyl cyanide, 127.8 g of triethylamine and 1200 ml of $CH_3CN$ is boiled at reflux for 20 hours and thereafter evaporated under reduced pressure. The oily residue is taken up in 1000 ml of EtOAc and the solution is washed with $CH_3COOH:H_2O$ 9:1 and then with $H_2O$. The EtOAc extracts are dried with $Na_2SO_4$. After evaporation of the solvent the residue is taken up in a mixture of $CH_3CN$ and $CF_3COOH$ (20:1), whereby a crystalline precipitate separates. There is thus obtained 4-tert-butyl-N-[2-(2-cyano-pyridin-4-yl)-6-(2-hydroxy-ethoxy)-5-(2-methoxy-phenoxy)-pyrimidin-4-yl]-benzenesulphonamide of melting point 176–179° C.

EXAMPLE 3

A suspension of 50.0 g of 4-tert-butyl-N-[2-(2-cyanopyridin-4-yl)-6-(2-hydroxy-ethoxy)-5-(2-methoxy-phenoxy)-pyrimidin-4-yl]-benzenesulphonamide, 46.33 g of $NH_4Cl$ and 56.47 g of $NaN_3$ in 1600 ml of DMF is heated to 70° C. for 24 hours while stirring vigorously. The majority of the solvent is distilled off under reduced pressure, the residue is dissolved in $H_2O$, the solution is extracted four times at pH 6.5 with ether, thereafter treated with $CH_3COOH$ to pH=4.5 and extracted with EtOAc. After working up there is obtained a residue which is treated with ether and filtered off under suction therefrom. There is thus obtained 4-tert-butyl-N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide, melting point 225–227° C.

EXAMPLE 4 a) To a solution, heated to 90° C., of 46.0 g of 4-tert-butyl-N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide in 600 ml of abs. dioxan is added dropwise within 60 minutes while stirring a cold solution of 22.0 g of 2-pyridylcarbonyl azide in 200 ml of dioxan. After 4 hours the solvent is evaporated under reduced pressure, the residue is taken up in 300 ml of EtOAc and left to stand at room temperature overnight. The crystalline mass is filtered off under suction and washed with EtOAc. After repeated recrystallization from tetrahydrofuran and EtOAc and drying under reduced pressure firstly at 45° C. for 3 days and thereafter at 65° C. for a further 2 days there is obtained 2-[6-(4-tert-butyl-phenylsulphonylamino)-5-(2-methoxy-phenoxy)-2-(2-1H-tetrazol-5-yl-pyridin-4-yl)-pyrimidin-4-yl-oxy]-ethyl pyridin-2-ylcarbamate, melting point from 214° C. with very slow decomposition.

b) The 2-pyridyl-carbonyl azide used as the starting material can be prepared as follows:

A solution of 53.9 g of 2-picolinic acid in 330 ml of abs. DMF and 61.2 ml of triethylamine is treated dropwise within 30 minutes at 10° C. with 99.7 ml of diphenylphosphoryl azide. After 2 hours at room temperature the solution is evaporated for the most part at 30° C. under reduced pressure, the oily residue is treated with 200 ml of a 5% sodium bicarbonate solution and exhaustively extracted with ether. The ethereal extracts are combined, dried with $MgSO_4$ and evaporated at room temperature under reduced pressure. The yellowish oily residue is cooled in an ice bath at 0–5° C. and the crystals are washed at −20° C. with a 1:1 mixture of ether and hexane. There is thus obtained 2-pyridylcarbonyl azide as colourless crystals of melting point 39–41° C.

EXAMPLE 5

A solution of 47.8 g of 2-[6-(4-tert-butyl-phenylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate in 500 ml of abs. THF is treated dropwise with a cold solution of 2.8 g of sodium in 50 ml of methanol, whereby there forms gradually a solid precipitate which, after stirring at room temperature for 1 hour, is filtered off under suction, dried under greatly reduced pressure at 35° C. for 3 days and thereafter at 50° C. for 2 days.

There is thus obtained the bis-sodium salt, decomposition point above 250° C.

EXAMPLE 6

The same tetrazole as in Example 3 is obtained starting from the same starting material as in Example 3 in a one-pot reaction (3 steps) under the following conditions:

2.4 ml of a 1.0N sodium methylate solution are added at room temperature to a suspension of 1.15 g (2 mmol) of 4-tert-butyl-N-[2-(2-cyano-pyridin-4-yl)-6-(2-hydroxy-ethoxy)-5-(2-methoxy-phenoxy)-pyrimidin-4-yl]-benzenesulphonamide in 50 ml of abs. MeOH. The clear yellowish solution which results therefrom is held at 40° C. for 3 days.

The solution of the iminoether is slowly added dropwise at room temperature within 30 minutes to a suspension of 302 mg (4.4 mmol) of $H_2N—NH_2 \cdot HCl$ in 10 ml of abs. MeOH, whereby a crystalline precipitate separates gradually. The suspension is cooled to 2° C. while stirring further and treated with 15 ml of 1.0N HCl. The clear yellowish solution (pH=1.7) is treated dropwise with a solution of 800 mg (11.6 mmol) of $NaNO_2$ in 10 ml of $H_2O$ in such a manner that the temperature does not exceed 5° C. (pH 2.7). After 1 hour a further 2 ml of 1N HCl are added and then a solution of 200 mg (2.9 mmol) of $NaNO_2$ in 2 ml of $H_2O$ is added. The solution is left at room temperature for 2 hours, the MeOH is evaporated under reduced pressure and the suspension remaining behind is extracted with EtOAc. The combined EtOAc solutions are firstly washed twice with $H_2O$ and thereafter carefully extracted with a 0.5N $NaHCO_3$—$H_2O$ solution. The combined aqueous ($NaHCO_3$) solutions are carefully treated with 3N HCl (to pH=2) and the suspension is extracted with EtOAc as usual. After evaporation of the solvent under reduced pressure there is obtained a crystalline residue which is identical with the product obtained in Example 3.

EXAMPLE 7 a) In analogy to Example 1a), from N-[6-chloro-5-(2-methoxy-phenoxy)-2-(1-oxy-pyridin-4-yl)-pyrimidin-4-yl]-benzenesulphonamide and Na glycolate in ethylene glycol there is obtained N-[6-(2-hydroxy-ethoxy)-5-(2-methoxy-phenoxy)-2-( 1-oxy-pyridin-4-yl)-pyrimidin-4-yl]-benzenesulphonamide, melting point 110–112° C. (from EtOAc).

b) In analogy to Example 2, from N-[6-(2-hydroxy-ethoxy)-5-(2-methoxy-phenoxy)-2-(1-oxy-pyridin-4-yl)-pyrimidin-4-yl]-benzenesulphonamide there is obtained N-[2-(2-cyano-pyridin-4-yl)-6-(2-hydroxy-ethoxy)-5-(2-methoxyphenoxy)-pyrimidin-4-yl]-benzenesulphonamide.

EXAMPLE 8 a) In analogy to Example 1a), from N-[6-chloro-5-(2-methoxy-phenoxy)-2-(1-oxy-pyridin-4-yl)-pyrimidin-4-yl]-4-methyl-benzenesulphonamide there is obtained N-[6-(2-hydroxy-ethoxy)-5-(2-methoxy-phenoxy)-2-(1 -oxy-pyridin-4-yl)-pyrimidin-4-yl]-4-methyl-benzenesulphonamide, melting point 172–173° C. (from EtOAc).

b) In analogy to Example 2, from N-[6-(2-hydroxy-ethoxy)-5-(2-methoxy-phenoxy)-2-(1-oxy-pyridin-4-yl)-pyrimidin-4-yl]-4-methyl-benzenesulphonamide there is obtained N-[2-(2-cyano-pyridin-4-yl)-6-(2-hydroxy-ethoxy)-5-(2-methoxy-phenoxy)-pyrimidin- 4-yl]-4-methyl-benzenesulphonamide.

EXAMPLE 9 a) In analogy to Example 1a), from N-[6-chloro-5-(2-methoxy-phenoxy)-2-(1-oxy-pyridin-4-yl)-pyrimidin-4-yl]-4-methoxy-benzenesulphonamide there is obtained N-[6-(2-hydroxy-ethoxy)-5-(2-methoxy-phenoxy)-2-(1-oxy-pyridin-4-yl)-pyrimidin-4-yl]-4-methoxy-benzenesulphonamide as a white solid.

b) In analogy to Example 2, from N-[6-(2-hydroxy-ethoxy)-5-(2-methoxy-phenoxy)-2-(1-oxy-pyridin-4-yl)-pyrimidin-4-yl]-4-methoxy-benzenesulphonic acid there is obtained N-[2-(2-cyano-pyridin-4-yl)-6-(2-hydroxy-ethoxy)-5-(2-methoxy-phenoxy)-pyrimidin-4-yl]-4-methoxy-benzenesulphonamide.

EXAMPLE 10 a) In analogy to Example 1a), from N-[6-chloro-5-(2-methoxy-phenoxy)-2-(1-oxy-pyridin-4-yl)-pyrimidin-4-yl]-4-methylsulphanyl-benzenesulphonamide there is obtained N-[6-(2-hydroxy-ethoxy)-5-(2-methoxy-phenoxy)-2-(1-oxy-pyridin-4-yl)-pyrimidin-4-yl]-4-methylsulphanyl-benzenesulphonamide, melting point 146–150° C. (from acetonitrile).

b) In analogy to Example 2, from N-[6-(2-hydroxy-ethoxy)-5-(2-methoxy-phenoxy)-2-(1-oxy-pyridin-4-yl)-pyrimidin-4-yl]-4-methylsulphanyl-benzenesulphonamide there is obtained N-[2-(2-cyano-pyridin-4-yl)-6-(2-hydroxy-ethoxy)-5-(2-methoxy-phenoxy)-pyrimidin-4-yl]-4-methylsulphanyl-benzenesulphonamide.

EXAMPLE 11 a) In analogy to Example 1a), from 1,3-benzodioxol-5-sulphonic acid 6-chloro-5-(2-methoxy-phenoxy)-2-(1-oxy-pyridin-4-yl)-pyrimidin-4-ylamide there is obtained 1,3-benzodioxol-5-sulphonic acid 6-(2-hydroxy-ethoxy)-5-(2-methoxy-phenoxy)-2-(1-oxy-pyridin-4-yl)-pyrimidin-4-ylamide, melting point 174–175° C. (from acetonitrile).

b) In analogy to Example 2, from 1,3-benzodioxol-5-sulphonic acid 6-(2-hydroxy-ethoxy)-5-(2-methoxy-phenoxy)-2-(1-oxy-pyridin-4-yl)-pyrimidin-4-ylamide there is obtained 1,3-benzodioxol-5-sulphonic acid 2-(2-cyano-pyridin-4-yl)-6-(2-hydroxy-ethoxy)-5-(2-methoxy-phenoxy)-pyrimidin-4-ylamide.

EXAMPLE 12 a) In analogy to Example 1a), from N-[6-chloro-5-(2-methoxy-phenoxy)-2-(1-oxy-pyridin-4-yl)-pyrimidin-4-yl]-3,4-dimethoxy-benzenesulphonamide there is obtained N-[6-(2-hydroxy-ethoxy)-5-(2-methoxy-phenoxy)-2-(1-oxy-pyridin-4-yl)-pyrimidin-4-yl]-3,4-dimethoxy-benzenesulphonamide, melting point 189–191° C. (from EtOAc).

b) In analogy to Example 2, from N-[6-(2-hydroxy-ethoxy)-5-(2-methoxy-phenoxy)-2-(1-oxy-pyridin-4-yl)-pyrimidin-4-yl]-3,4-dimethoxy-benzenesulphonamide there is obtained N-[2-(2-cyano-pyridin-4-yl)-6-(2-hydroxy-ethoxy)-5-(2-methoxy-phenoxy)-pyrimidin-4-yl]-3,4-dimethoxy-benzenesulphonamide.

EXAMPLE 13 a) In analogy to Example 1a), from N-[6-chloro-5-(2-methoxy-phenoxy)-2-(1-oxy-pyridin-4-yl)-pyrimidin-4-yl]-2,5-dimethoxy-benzenesulphonamide there is obtained N-[6-(2-hydroxy-ethoxy)-5-(2-methoxy-phenoxy)-2-(1-oxy-pyridin-4-yl)-pyrimidin- 4-yl]-2,5-dimethoxy-benzenesulphonamide as a white solid.

b) In analogy to Example 2, from N-[6-(2-hydroxy-ethoxy)-5-(2-methoxy-phenoxy)-2-(1-oxy-pyridin-4-yl)-pyrimidin-4-yl]-2,5-dimethoxy-benzenesulphonamide there is obtained N-[2-(2-cyano-pyridin-4-yl)-6-(2-hydroxy-ethoxy)-5-(2-methoxy-phenoxy)-pyrimidin-4-yl]-2,5-dimethoxy-benzenesulphonamide.

EXAMPLE 14 a) In analogy to Example 1a), from pyridine-3-sulphonic acid 6-chloro-5-(2-methoxy-phenoxy)-2-(1-oxy-pyridin-4-yl)-pyrimidin-4-ylamide there is obtained pyridine-3-sulphonic acid 6-(2-hydroxy-ethoxy)-5-(2-methoxy-phenoxy)-2-(1-oxy-pyridin-4-yl)-pyrimidin-4-ylamide, melting point 227–228° C. (from EtOAc).

b) In analogy to Example 2, from pyridine-3-sulphonic acid 6-(2-hydroxy-ethoxy)-5-(2-methoxy-phenoxy)-2-(1-oxy-pyridin-4-yl)-pyrimidin-4-ylamide there is obtained pyridine-3-sulphonic acid 2-(2-cyano-pyridin-4-yl)-6-(2-hydroxy-ethoxy)-5-(2-methoxy-phenoxy)-pyrimidin-4-ylamide.

EXAMPLE 15 a) In analogy to Example 1a), from 5-methyl-pyridine-2-sulphonic acid 6-chloro-5-(2-methoxy-phenoxy)-2-(1-oxy-pyridin-4-yl)-pyrimidin-4-ylamide there is obtained 5-methyl-pyridine-2-sulphonic acid 6-(2-hydroxy-ethoxy)-5-(2-methoxy-phenoxy)-2-(1-oxy-pyridin-4-yl)-pyrimidin-4-ylamide, melting point 188–190° C. (from acetonitrile).

b) In analogy to Example 2, from 5-methyl-pyridine-2-sulphonic acid 6-(2-hydroxy-ethoxy)-5-(2-methoxy-phenoxy)-2-(1-oxy-pyridin-4-yl)-pyrimidin-4-ylamide there is obtained 5-methyl-pyridine-2-sulphonic acid 2-(2-cyano-pyridin-4-yl)-6-( 2-hydroxy-ethoxy)-5-(2-methoxy-phenoxy)-pyrimidin-4-ylamide.

EXAMPLE 16 a) In analogy to Example 1a), from 5-isopropyl-pyridine-2-sulphonic acid 6-chloro-5-(2-methoxy-phenoxy)-2-(1-oxy-pyridin-4-yl)-pyrimidin-4-ylamide there is obtained 5-iso-propyl-pyridine-2-sulphonic acid 6-(2-hydroxy-ethoxy)-5-(2-methoxy-phenoxy)-2-(1-oxy-pyridin-4-yl)-pyrimidin-4-ylamide, melting point 140–141° C. (from EtOAc).

b) In analogy to Example 2, from 5-isopropyl-pyridine-2-sulphonic acid 6-(2-hydroxy-ethoxy)-5-(2-methoxy-phenoxy)-2-(1-oxy-pyridin-4-yl)-pyrimidin-4-ylamide there is obtained 5-isopropyl-pyridine-2-sulphonic acid 2-(2-cyano-pyridin-4-yl)-6-(2-hydroxy-ethoxy)-5-(2-methoxy-phenoxy)-pyrimidin-4-ylamide.

EXAMPLE 17 a) In analogy to Example 1a), from 4-tert-butyl-N-[6-chloro-5-(2-chloro)-5-methoxy-phenoxy)-2-(1-oxy-pyridin-4-yl)-pyrimidin-4-yl]-benzenesulphonamide there is obtained 4-tert-butyl-N-[5-(2-chlor-5-methoxy-phenoxy)-6-(2-hydroxy-ethoxy)-2-(1-oxy-pyridin-4-yl)-pyrimidin-4-yl]-benzenesulphonamide, melting point 228–230° C. (from EtOAc).

b) In analogy to Example 2, from 4-tert-butyl-N-[5-(2-chloro-5-methoxy-phenoxy)-6-(2-hydroxy-ethoxy)-2-(1-oxy-pyridin-4-yl)-pyrimidin-4-yl]-benzenesulphonamide there is obtained 4-tert-butyl-N-[5-(2-chloro-5-methoxy-phenoxy)-2-(2-cyano-pyridin-4-yl)-6-(2-hydroxy-ethoxy)-pyrimidin-4-yl]-benzenesulphonamide.

EXAMPLE 18 a) In analogy to Example 1a), from 1,3-benzodioxol-4-sulphonic acid 6-chloro-5-(2-chloro-5-methoxy-phenoxy)-2-(1-oxy-pyridin-4-yl)-pyrimidin-4-ylamide there is obtained 1,3-benzodioxol-4-sulphonic acid 5-(2-chloro-5-methoxy-phenoxy)-6-(2-hydroxy-ethoxy)-2-(1-oxy-pyridin-4-yl)-pyrimidin-4-ylamide, melting point 208–210° C. (from EtOAc).

b) In analogy to Example 2, from 1,3-benzodioxol-4-sulphonic acid 5-(2-chloro-5-methoxy-phenoxy)-6-(2-hydroxy-ethoxy)-2-(1-oxy-pyridin-4-yl)-pyrimidin-4-ylamide there is obtained 1,3-benzodioxol-5-sulphonic acid 5-(2-chloro-5-methoxy-phenoxy)-2-(2-cyano-pyridin-4-yl)-6-(2-hydroxy-ethoxy)-pyrimidin-4-ylamide.

EXAMPLE 19 a) In analogy to Example 1a), from 5-isopropyl-pyridine-2-sulphonic acid-6-chloro-5-(2-chloro-5-methoxy-phenoxy)-2-(1-oxy-pyridin-4-yl)-pyrimidin-4-ylamide there is obtained 5-1 isopropyl-pyridine-2-sulphonic acid-5-(2-chloro-5-methoxy-phenoxy)-6-(2-hydroxy-ethoxy)-2-(1-oxy-pyridin-4-yl)-pyrimidin-4-ylamide, melting point 204–206° C. (from EtOAc).

b) In analogy to Example 2 from 5-isopropyl-pyridine-2-sulphonic acid 5-(2-chloro-5-methoxy-phenoxy)-6-(2-hydroxy-ethoxy)-2-(1-oxy-pyridin-4-yl)-pyrimidin-4-ylamide there is obtained 5-isopropyl-pyridine-2-sulphonic acid 5-(2-chloro-5-methoxy-phenoxy)-2-(2-cyano-pyridin-4-yl)-6-(2-hydroxy-ethoxy)-pyrimidin-4-ylamide.

EXAMPLE 20 a) In analogy to Example 1a), from 2-[4-(4-tert-butyl-phenylsulphonylamino)-6-chloro-5-(2-methoxy-phenoxy)-pyrimidin-2-yl]-pyridine 1-oxide there is obtained 2-[4-(4-tert-butyl-phenylsulphonylamino)-6-(2-hydroxy-ethoxy)-5-(2-methoxy-phenoxy)-pyrimidin- 2-yl]-pyridine 1-oxide as an amorphous substance.

b) In analogy to Example 2 from 2-[4-(4-tert-butyl-phenylsulphonylamino)-6-(2-hydroxy-ethoxy)-5-(2-methoxy-phenoxy)-pyrimidin-2-yl]-pyridine 1-oxide there is obtained 4-tert-butyl-N-[2-(6-cyano-pyridin-2-yl)-6-(2-hydroxy-ethoxy)-5-(2-methoxy-phenoxy)-pyrimidin-4-yl]-benzenesulphonamide.

EXAMPLE 21

In analogy to Example 3, from N-[2-(2-cyano-pyridin-4-yl)-6-(2-hydroxy-ethoxy)-5-(2-methoxy-phenoxy)-pyrimidin-4-yl]-benzenesulphonamide there is obtained N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide as a white substance of melting point 205–207° C. from acetonitrile.

EXAMPLE 22

In analogy to Example 3, from N-[2-(2-cyano-pyridin-4-yl)-6-(2-hydroxy-ethoxy)-5-(2-methoxy-phenoxy)-pyrimidin-4-yl]-4-methyl-benzenesulphonamide there is obtained N-[6-(2-hydroxy-ethoxy)-5-(2-methoxy-phenoxy)-2-(2-1H-tetrazol-5-yl-pyridin-4-yl)-pyrimidin-4-yl]-4-methyl-benzenesulphonamide as a white substance of melting point 214–216° C. from CH$_3$CN.

EXAMPLE 23

In analogy to Example 3, from N-[2-(2-cyano-pyridin-4-yl)-6-(2-hydroxy-ethoxy)-5-(2-methoxy-phenoxy)-pyrimidin-4-yl]-4-methoxy-benzenesulphonamide there is obtained N-[6-(2-hydroxy-ethoxy)-5-(2-methoxyphenoxy)-2-(2-1H-tetrazol-5-yl-pyridin-4-yl)-pyrimidin-4-yl]-4-methoxy-benzenesulphonamide as a white substance of melting point 218–220° C. from acetonitrile.

EXAMPLE 24

In analogy to Example 3, from N-[2-(2-cyano-pyridin-4-yl)-6-(2-hydroxy-ethoxy)-5-(2-methoxy-phenoxy)-pyrimidin-4-yl]-4-methylsulphanyl-benzenesulphonamide there is obtained N-[6-(2-hydroxy-ethoxy)-5-(2-methoxy-phenoxy)-2-(2-1H-tetrazol-5-yl-pyridin-4-yl)-pyrimidin-4-yl]-4-methylsulphanyl-benzene-sulphonamide as a white substance.

EXAMPLE 25

In analogy to Example 3, from 1,3-benzodioxol-5-sulphonic acid 2-(2-cyano-pyridin-4-yl)-6-(2-hydroxy-ethoxy)-5-(2-methoxy-phenoxy)-pyrimidin-4-ylamid there is obtained 1,3-benzodioxol-5-sulphonic acid 6-(2-hydroxy-ethoxy)-5-(2-methoxy-phenoxy)-2-(2-1H-tetrazol-5-yl-pyridin-4-yl)-pyrimidin-4-ylamide as a white substance of melting point 227–229° C. from $CH_3CN$.

EXAMPLE 26

In analogy to Example 3, from N-[2-(2-cyano-pyridin-4-yl)-6-(2-hydroxy-ethoxy)-5-(2-methoxy-phenoxy)-pyrimidin-4-yl]-3,4-dimethoxy-benzenesulphonamide there is obtained N-[6-(2-hydroxy-ethoxy)-5-(2-methoxy-phenoxy)-2-(2-1H-tetrazol-5-yl-pyridin-4-yl)-pyrimidin-4-yl]-3,4-dimethoxy-benzenesulphonamide as a white substance of melting point 224–225° C. from acetonitrile.

EXAMPLE 27

In analogy to Example 3, from N-[2-(2-cyano-pyridin-4-yl)-6-(2-hydroxy-ethoxy)-5-(2-methoxy-phenoxy)-pyrimidin-4-yl]-2,5-dimethoxy-benzenesulphonamide there is obtained N-[6-(2-hydroxy-ethoxy)-5-(2-methoxy-phenoxy)-2-(2-1H-tetrazol-5-yl-pyridin-4-yl)-pyrimidin-4-yl]-2,5-dimethoxy-benzenesulphonamide as a white substance.

EXAMPLE 28

In analogy to Example 3, from pyridine-3-sulphonic acid 2-(2-cyano-pyridin-4-yl)-6-(2-hydroxy-ethoxy)-5-(2-methoxy-phenoxy)-pyrimidin-4-ylamide there is obtained pyridine-3-sulphonic acid 6-(2-hydroxy-ethoxy)-5-(2-methoxy-phenoxy)-2-(2-1H-tetrazol-5-yl-pyridin-4-yl)-pyrimidin-4-ylamide as a white substance.

EXAMPLE 29

In analogy to Example 3, from 5-methyl-pyridine-2-sulphonic acid 2-(2-cyano-pyridin-4-yl)-6-(2-hydroxy-ethoxy)-5-(2-methoxy-phenoxy)-pyrimidin-4-ylamide there is obtained 5-methyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide as a white substance of melting point 239–241° C. from $CH_3CN$.

EXAMPLE 30

In analogy to Example 3, from 5-isopropyl-pyridine-2-sulphonic acid 2-(2-cyano-pyridin-4-yl)-6-(2-hydroxy-ethoxy)-5-(2-methoxy-phenoxy)-pyrimidin-4-ylamide there is obtained 5-isopropyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide as a white substance of melting point 198–200° C. from acetonitrile. The corresponding disodium salt is obtained as a white powder from this product using sodium methylate in analogy to Example 5.

EXAMPLE 31

In analogy to Example 3, from 4-tert-butyl-N-[5-(2-chloro-5-methoxy-phenoxy)-[2-(2-cyano-pyridin-4-yl]-6-(2-hydroxy-ethoxy)-pyrimidin-4-yl]-benzenesulphonamide there is obtained 4-tert-butyl-N-[5-(2-chloro-5-methoxy-phenoxy)-6-(2-hydroxy-ethoxy)-2-(2-1H-tetrazol-5-yl-pyridin-4-yl)-pyrimidin-4-yl]-benzenesulphonamide of melting point 170–172° C. from $CH_3CN$. The corresponding disodium salt is obtained as a white powder from this product using sodium methylate in analogy to Example 5.

EXAMPLE 32

In analogy to Example 3, from 1,3-benzodioxol-5-sulphonic acid 5-(2-chloro-5-methoxy-phenoxy)-2-(2-cyano-pyridin-4-yl)-6-(2-hydroxy-ethoxy)-pyrimidin-4-ylamide there is obtained 1,3-benzodioxol-5-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide.

EXAMPLE 33

In analogy to Example 3, from 5-isopropyl-pyridine-2-sulphonic acid 5-(2-chloro-5-methoxy-phenoxy)-2-(2-cyano-pyridin-4-yl)-6-(2-hydroxy-ethoxy)-pyrimidin-4-ylamide there is obtained 5-isopropyl-pyridine-2-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide.

EXAMPLE 34

In analogy to Example 3, from 4-tert-butyl-N-[2-(6-cyano-pyridin-2-yl)-6-(2-hydroxy-ethoxy)-5-(2-methoxy-phenoxy)-pyrimidin-4-yl]-benzenesulphonamide there is obtained 4-tert-butyl-N-[6-(2-hydroxy-ethoxy)-5-(2-methoxy-phenoxy)-2-[6-(1H-tetrazol-5-yl)-pyridin-2-yl]-pyrimidin-4-yl]-benzene-sulphonamide of melting point 248–251° C. (with decomposition) from $CH_2Cl_2+CH_3CN$.

EXAMPLE 35

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide and 2-pyridyl-carbonyl azide there is obtained 2-[5-(2-methoxy-phenoxy)-6-phenyl-sulphonylamino-2-(2-1H-tetrazol-5-yl-pyridin-4-yl)-pyrimidin-4-yloxy]-ethyl pyridin-2-ylcarbamate as a white substance.

EXAMPLE 36

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-4-methyl-benzenesulphonamide and 2-pyridylcarbonyl azide there is obtained 2-[5-(2-methoxy-phenoxy)-6-(4-methyl-phenylsulphonylamino)-2-(2-1H-tetrazol-5-yl-pyridin-4-yl)-pyrimidin-4-yloxy]-ethyl pyridin-2-ylcarbamate as a white substance of melting point 224–225° C. from $CH_3CN$.

EXAMPLE 37

In analogy to Example 4, from N-[6-(2-hydroxy-ethoxy)-5-(2-methoxy-phenoxy)-2-(2-1H-tetrazol-5-yl-pyridin-4- yl)-pyrimidin-4-yl]-4-methyl-benzenesulphonamide and 3,4-methylenedioxy-phenyl-carbonyl azide there is obtained 2-[5-(2-methoxy-phenoxy)-6-(4-methylphenylsulphonylamino)-2-(2-1H-tetrazol-5-yl-pyridin-4-yl)-pyrimidin-4-yloxy]-ethyl 1,3-benzodioxol-5-ylcarbamate of melting point 198–199° C. from $CH_3CN$.

EXAMPLE 38

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-4-methoxy-benzenesulphonamide and 2-pyridylcarbonyl azide there is obtained 2-[5-(2-methoxy-phenoxy)-6-(4-methoxy-phenylsulphonylamino-2-(2-1H-tetrazol-5-yl-pyridin-2-yl)-pyrimidin-4-yloxy]-ethyl pyridin-2-ylcarbamate of melting point 224–225° C. from EtOAc.

EXAMPLE 39

In analogy to Example 4, from N-[6-(2-hydroxy-ethoxy)-5-(2-methoxy-phenoxy)-2-(2-1H-tetrazol-5-yl-pyridin-4-yl)-pyrimidin- 4-yl]-4-methoxy-benzenesulphonamide and 3,4-methylenedioxy-phenylcarbonyl azide there is obtained 2-[5-(2-methoxy-phenoxy)-6-(4-methoxy-phenylsulphonylamino)-2-(2-1H-tetrazol-5-yl-pyridin-4-yl)-pyrimidin-4-yloxy]-ethyl 1,3-benzodioxol-5-ylcarbamate of melting point 198–200° C. from EtOAc.

EXAMPLE 40

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-4-methylsulphanyl-benzenesulphonamide and 2-pyridylcarbonyl azide there is obtained 2-[5-(2-methoxy-phenoxy)-6-(4-methylsulphanylphenylsulphonylamino)-2-(2-1H-tetrazol-5-yl-pyridin-4-yl)-pyrimidin-4-yloxy]-ethyl pyridin-2-ylcarbamate.

EXAMPLE 41

In analogy to Example 4, from 1,3-benzodioxol-5-sulphonic acid 6-(2-hydroxy-ethoxy)-5-(2-methoxy-phenoxy)-2-(2-1H-tetrazol-5-yl-pyridin-4-yl)-pyrimidin-4-ylamide and 2-pyridylcarbonyl azide there is obtained 2-[6-(1,3-benzodioxol-5-yl-sulphonylamino)-5-(2-methoxy-phenoxy)-2-(2-1H-tetrazol-5-yl-pyridin-4-yl)-pyrimidin-4-yloxy]-ethyl pyridin-2-ylcarbamate of melting point 194–196° C. from EtOAc.

EXAMPLE 42

In analogy to Example 4, from 1,3-benzodioxol-5-sulphonic acid 6-(2-hydroxy-ethoxy)-5-(2-methoxy-phenoxy)-2-(2-1H-tetrazol-5-yl-pyridin-4-yl)-pyrimidin-4-ylamide and 3,4-methylenmdioxy-phenyl-carbonyl azide there is obtained 2-[6-(1,3-benzodioxol-5-ylsulphonylamino)-5-(2-methoxy-phenoxy)-2-(2-1H-tetrazol-5-yl-pyridin-4-yl)-pyrimidin-4-yloxy]-ethyl 1,3-benzodioxol-5-ylcarbamate of melting point 187–188° C. from EtOAc.

EXAMPLE 43

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-3,4-dimethoxy-benzenesulphonamide and 2-pyridylcarbonyl azide there is obtained 2-[6-(3,4-dimethoxy-phenylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate.

EXAMPLE 44

In analogy to Example 4, from N-[6-(2-hydroxy-ethoxy)-5-(2-methoxy-phenoxy)-2-(2-1H-tetrazol-5-yl-pyridin-4-yl)-pyrimidin-4-yl]-2,5-dimethoxy-benzenesulphonamide and 2-pyridylcarbonyl azide there is obtained 2-[5-(2-methoxy-phenoxy)-6-(2,5-dimethoxy-phenylsulphonylamino)-2-(2-1H-tetrazol-5-yl-pyridin-4-yl)-pyrimidin-2-yloxy]-ethyl pyridin-2-ylcarbamate.

EXAMPLE 45

In analogy to Example 4, from pyridine-3-sulphonic acid 6-(2-hydroxy-ethoxy)-5-(2-methoxy-phenoxy)-2-(2-1H-tetrazol-5-yl-pyridin-4-yl)-pyrimidin-4-ylamide and 2-pyridylcarbonyl azide there is obtained 2-[5-(2-methoxy-phenoxy)-2-(2-1H-tetrazol-5-yl-pyridin-4-yl)-6-pyridin-3-ylsulphonylamino-pyrimidin4-yloxy]-ethyl pyridin-2-ylcarbamate.

EXAMPLE 46

In analogy to Example 4, from pyridine-3-sulphonic acid 6-(2-hydroxy-ethoxy)-5-(2-methoxy-phenoxy)-2-(2-1H-tetrazol-5-yl-pyridin-4-yl)-pyrimidin-4-ylamide and 3,4-methylenedioxy-phenyl-carbonyl azide there is obtained 2-[5-(2-methoxy-phenoxy)-6-pyridin-3-ylsulphonylamino-2-(2-1H-tetrazol-5-yl-pyridin-4-yl)-pyrimidin-4-yloxy]-ethyl 1,3-benzodioxol-5-ylcarbamate.

EXAMPLE 47

In analogy to Example 4, from 5-methyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide and 2-pyridylcarbonyl azide there is obtained 2-[5-(2-methoxy-phenoxy)-6-(5-methyl-pyridin-2-ylsulphonylamino)-2-(2-1H-tetrazol-5-yl-pyridin-4-yl)-pyrimidin-4-yloxy]-ethyl pyridin-2-ylcarbamate.

EXAMPLE 48

In analogy to Example 4 from 5-isopropyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide and 2-pyridylcarbonyl azide there is obtained 2-[6-(5-isopropyl-pyridin-2-ylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate.

EXAMPLE 49

In analogy to Example 4, from 5-isopropyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide and 3,4-methylenedioxy-phenyl-carbonyl azide there is obtained 2-[6-(5-isopropyl-pyridin-2-ylsulphonylamino)-5-(2-methoxy-phenoxy)-2-(2-1H-tetrazol-5-yl-pyridin-4-yl)-pyrimidin-4-yloxy]-ethyl 1,3-benzodioxol-5-ylcarbamate.

EXAMPLE 50

In analogy to Example 4, from 4-tert-butyl-N-[5-(2-chloro-5-methoxy-phenoxy)-6-(2-hydroxy-ethoxy)-2-(2-1H-tetrazol-5-yl-pyridin-4-yl)-pyrimidin-4-yl]-benzenesulphonamide and 2-pyridylcarbonyl azide there is obtained 2-[6-(4-tert-butyl-phenylsulphonylamino)-5-(2- chloro-5-methoxy-phenoxy)-2-(2- 1H-tetrazol-5-yl-pyridin-4-yl)-pyrimidin-4-yloxy]-ethyl pyridin-2-ylcarbamate.

EXAMPLE 51

In analogy to Example 4, from 1,3-benzodioxol-5-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide and 2-pyridylcarbonyl azide there is obtained 2-[6-(1,3-benzodioxol-5-ylsulphonylamino)-5-(2-chloro-5-methoxy-phenoxy)-2-(2-1H-tetrazol-5-yl-pyridin-4-yl)-pyrimidin-4-yloxy]-ethyl pyridin-2-ylcarbamate.

EXAMPLE 52

In analogy to Example 4, from 5-isopropyl-pyridine-2-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide there is obtained 2-[5-(2-chloro-5-methoxy-phenoxy)-6-(5-isopropyl-pyridin-2-ylsulphonylamino]-2-(2-1H-tetrazol-5-yl-pyridin-2-yl)-pyrimidin-4-yloxy]-ethyl pyridin-2-yl-carbamate.

EXAMPLE 53

In analogy to Example 4, from 4-tert-butyl-N-[6-(2-hydroxy-ethoxy)-5-(2-methoxy-phenoxy)-2-[6-(1H-tetrazol-5-yl)-pyridin-2-yl]-pyrimidin-4-yl]-benzenesulphonamide there is obtained 2-[6-(4-tert-butyl-phenylsulphonylamino)-5-(2-methoxy-phenoxy)-2-(2-1H-tetrazol-5-yl-pyridin-2-yl)-pyrimidin-4-yloxy]-ethyl pyridin-2-ylcarbamate.

EXAMPLE 54

In analogy to Example 1, from benzyloxy-ethanol Na with 4-[4-(4-tert-butyl-phenylsulphonylamino)-6-chloro-5-(2-methoxy-phenoxy)-pyrimidin-2-yl]-pyridine 1-oxide there is obtained N-[6-(2-benzyloxy-ethoxy)-5-(2-methoxy-phenoxy)-2-(1-oxy-pyridin- 4-yl)-pyrimidin-4-yl]-4-tert-butyl-benzenesulphonamide of melting point 170–171° C. from CH$_3$CN and therefrom with tri-methylsilyl cyanide in boiling triethylamine in analogy to Example 1, paragraph a), there is obtained N-[6-(2-benzyloxy-ethoxy)-2-(2-cyano-pyridin-4-yl)-5-(2-methoxy-phenoxy)-pyrimidin-4-yl]-4-tert-butyl-benzenesulphonamide.

EXAMPLE 55

In analogy to Example 3, from N-[6-(2-benzyloxy-ethoxy)-2-(2-cyano-pyridin-4-yl)-5-(2-methoxy-phenoxy)-pyrimidin-4-yl]-4-tert-butyl-benzenesulphonamide there is obtained N-[6-(2-benzyloxy-ethoxy)-5-(2-methoxy-phenoxy)-2-(2-1H-tetrazol-5-yl-pyridin-4-yl)-pyrimidin-4-yl]-4-tert-butyl-benzenesulphonamide as an amorphous substance of melting point 173–175° C.

EXAMPLE 56

In analogy to Example 1, from benzyloxy-ethanol sodium and 5-methyl-pyridine-2-sulphonic acid 6-chloro-5-(2-methoxy-phenoxy)-2-(1-oxy-pyridin-4-yl)-pyrimidin-4-ylamide there is obtained 5-methyl-pyridine-2-sulphonic acid [6-(2-benzyloxy-ethoxy)-5-(2-methoxy-phenoxy)-2-(1-oxy-pyridin-4-yl)-pyrimidin-4-yl]-amide, melting point 206–208° C. from CH$_3$CN, and therefrom with trimethylsilyl cyanide in boiling triethylamine in analogy to Example 2 there is obtained the corresponding nitrile, 5-methylpyridine-2-sulphonic acid-N-[6-(2-benzyloxy-ethoxy)-2-(2-cyanopyridin-4-yl)-5-(2-methoxyphenoxy)-pyrimidin-4-yl]-amide.

EXAMPLE 57

In analogy to Example 3, from the nitrile of Example 56 there is obtained 5-methyl-pyridine-2-sulphonic acid [6-(2-benzyloxy-ethoxy)-5-(2-methoxy-phenoxy)-2-(2-1H-tetrazol-5-yl-pyridin-4-yl]-amide, melting point 202–204° C. from CH$_3$CN.

EXAMPLE 58

In analogy to Example 1, from benzyloxy-ethanol sodium and 5-isopropyl-pyridine-2-sulphonic acid 6-chloro-5-(2-methoxy-phenoxy)-2-(1-oxy-pyridin-4-yl)-pyrimidin-4-ylamide there is obtained 5-isopropyl-pyridine-2-sulphonic acid [6-(2-benzyloxy-ethoxy)-5-(2-methoxy-phenoxy)-2-(1-oxy-pyridin-4-yl)-pyrimidin-4-yl]-amide and therefrom with trimethylsilyl cyanide in boiling triethylamine in analogy to Example 2 there is obtained the corresponding nitrile, 5-isopropylpyridine-2-sulphonic acid N-[6-(2-benzyloxy-ethoxy)-2-(2-cyanopyridin-4-yl)-5-(2-methoxyphenoxy)-pyrimidin-4-yl]-amide.

EXAMPLE 59

In analogy to Example 3, from 4-isopropyl-N-[2-(2-cyano-pyridin-4-yl)-6-(2-hydroxy-ethoxy)-5-(2-methoxy-phenoxy)-pyrimidin-4-yl]benzenesulphonamide there is obtained 5-iso-propyl-pyridine-2-sulphonic acid [6-(2-benzyloxy-ethoxy)-5-(2-methoxy-phenoxy)-2-[2-(1H-tetrazol-5-yl)-pyridin-4-yl]-pyrimidin-4-yl]-amide of melting point 236–237° C. from CH$_3$CN.

EXAMPLE 60

In analogy to Example 6, from 4-tert-butyl-N-[2-(2-cyanopyridin-4-yl)-6-(2-hydroxy-ethoxy)-5-(2-methoxy-phenoxy)-pyrimidin-4-yl]-benzenesulphonamide there is obtained the corresponding iminoether and therefrom with NH$_4$Cl in CH$_3$OH at room temperature there is obtained 4-tert-butyl-N-[2-[2-(amino-imino-methyl)-pyridin-4-yl]-6-(2-hydroxy-ethoxy)-5-(2-methoxy-phenoxy)-pyrimidin-4-yl]-benzenesulphonamide.

EXAMPLE 61

In analogy to Example 6, from 4-tert-butyl-N-[2-(2-cyanopyridin-4-yl)-6-(2-hydroxy-ethoxy)-5-(2-methoxy-phenoxy)-pyrimidin-4-yl]-benzenesulphonamide there is obtained the corresponding iminoether and therefrom with NH$_2$OH·HCl in CH$_3$OH at room temperature there is obtained 4-tert-butyl-N-[2-[2-(hydroxyamino-imino-methyl)-pyridin-4-yl]-6-(2-hydroxy-ethoxy)-5-(2-methoxy-phenoxy)-pyrimidin-4-yl]-benzene-sulphonamide.

EXAMPLE 62

In analogy to Example 6, from 4-tert-butyl-N-[2-(2-cyanopyridin-4-yl)-6-(2-hydroxy-ethoxy)-5-(2-methoxy-phenoxy)-pyrimidin-4-yl]-benzenesulphonamide there is obtained the corresponding iminoether and therefrom with 3N HCl at room temperature there is obtained ethyl 4-[4-(4-tert-butyl-phenyl-sulphonylamino)-6-(2-hydroxy-ethoxy)-5-(2-methoxy-phenoxy)-pyrimidin-2-yl]-pyridine-2-carboxylate.

EXAMPLE 63

By treating the ester prepared in Example 62 with 1N methanolic sodium hydroxide solution at room temperature and acidifying the reaction solution with acetic acid there is obtained the corresponding 4-[4-(4-tert-butylphenylsulphonylamino)-6-(2-hydroxy-ethoxy)-5-(2-methoxy-phenoxy)-pyrimidin-2-yl]-pyridine-2-carboxylic acid.

EXAMPLE 64 a) In analogy to Example 1, from 4-tert.-butyl-N-[6-chloro-2-(3-cyano-phenyl)-5-(2-methoxy-phenoxy)-pyrimidin-4-yl]-benzenesulphonamide and ethylene glycol sodium salt there is obtained 4-tert.-butyl-N-[2-(3-cyano-phenyl)-6-(2-hydroxy-ethoxy)-5-(2-methoxy-phenoxy)-pyrimidin-4-yl]-benzene-sulphonamide as a white product of melting point 197–198° C. from EtOAc.

Preparation of the starting material:

In analogy to Example 1 b), from 1,3-dicyanobenzene and sodium methylate in methanol followed by ammonium chloride there is obtained 3-cyano-benzamidine hydrochloride and therefrom with diethyl (2-methoxy-phenoxy) malonate there is obtained rac.-3-[5-(2-methoxy-phenoxy)-4,6-dioxo-1,4,5,6-tetrahydro-pyrimidin-2-yl]-benzonitrile as a white product. From this compound with $PCl_5$ and $POCl_3$ there is obtained 3-[4,6-dichloro-5-(2-methoxy-phenoxy)-pyrimidin-2-yl]-benzonitrile with a melting point of 155–156° from EtOAc. Reaction with 4-tert.-butylbenzenesulphonamide K yields 4-tert.-butyl-N-[6-chloro-2-(3-cyanophenyl)-5-(2-methoxyphenoxy)-pyrimidin-4-yl]-benzenesulphonamide.

EXAMPLE 65

In analogy to Example 3, from 4-tert.-butyl-N-[2-(3-cyanophenyl)-6-(2-hydroxy-ethoxy)-5-(2-methoxy-phenoxy)-pyrimidin-4-yl]-benzenesulphonamide, sodium azide and ammonium chloride in DMF there is obtained 4-tert.-butyl-N-[6-(2-hydroxy-ethoxy)-5-(2-methoxy-phenoxy)-2-(3-1H-tetrazol-5-yl-phenyl)-pyrimidin-4-yl]-benzenesulphonamide as a solid.

EXAMPLE 66

In analogy to Example 4, from 4-tert.-butyl-N-[6-(2-hydroxy-ethoxy)-5-(2-methoxy-phenoxy)-2-(3-1H-tetrazol-5-yl-phenyl)-pyrimidin-4-yl]-benzenesulphonamide and α-pyridylcarbonyl azide there is obtained 2-[6-(4-tert.-butyl-phenyl-sulphonyl)-5-(2-methoxy-phenoxy)-2-(3-1H-tetrazol-5-yl-phenyl)-pyrimidin-4-yloxy]-ethyl pyridin-2-ylcarbamate of melting point 138–139° C.

EXAMPLE 67

In analogy to Example 1, from 4-tert.-butyl-N-[6-chloro-2-(3-cyano-phenyl)-5-(2-methoxy-phenoxy)-pyrimidin-4-yl]-benzenesulphonamide and benzyloxy-ethanol sodium salt there is obtained N-[6-(2-benzyloxy-ethoxy)-2-(3-cyano-phenyl)-5-(2-methoxy-phenoxy)-pyrimidin-4-yl]-4-tert.-butyl-benzene-sulphonamide as a solid material of melting point 120–122° C. from EtOAc.

EXAMPLE 68

In analogy to Example 3, from N-[6-(2-benzyloxy-ethoxy)-2-(3-cyano-phenyl)-5-(2-methoxy-phenoxy)-pyrimidin-4-yl]-4-tert.-butyl-benzenesulphonamide, sodium azide and ammonium chloride in DMF there is obtained N-[6-(2-benzyloxy-ethoxy)-5-(2-methoxy-phenoxy)-2-(3-1H-tetrazol-5-yl-phenyl)-pyrimidin-4-yl]-4-tert.-butyl-benzenesulphonamide as a lighy yellow foam.

EXAMPLE 69

In analogy to Example 1, from 4-tert.-butyl-N-[6-chloro-2-(4-cyano-phenyl)-5-(2-methoxy-phenoxy)-pyrimidin-4-yl]-benzenesulphonamide and ethylene glycol sodium salt there is obtained 4-tert.-butyl-N-[2-(4-cyano-phenyl)-6-(2-hydroxy-ethoxy)-5-(2-methoxy-phenoxy)-pyrimidin-4-yl]-benzene-sulphonamide as a light brownish material of melting point 169–170° C. from EtOAc.

Preparation of the starting material:

From 1,4-dicyanobenzene and sodium methylate in methanol followed by ammonium chloride there is obtained 4-cyano-benzamidine hydrochloride, which is used in the next step without further purification, and therefrom with diethyl (2-methoxy-phenoxy)-malonate there is obtained rac.-4-[5-(2-methoxy-phenoxy)-4,6-dioxo-1,4,5,6-tetrahydro-pyrimidin-2-yl]-benzo-nitrile as a yellow product with a melting point >250° C. With $PCl_5$ and $POCl_3$ this compound yields 4-[4,6-dichloro-5-(2-methoxy-phenoxy)-pyrimidin-2-yl]-benzonitrile as a brownish material of melting point 179–180° C. from EtOAc. Reaction with 4-tert.-butyl-benzenesulphonamide K finally yields 4-tert.-butyl-N-[6-chloro-2-(4-cyanophenyl)-5-(2-methoxy-phenoxy)-pyrimidin-4-yl]-benzenesulphonamide.

EXAMPLE 70

In analogy to Example 3, from 4-tert.-butyl-N-[2-(4-cyano-phenyl)-6-(2-hydroxy-ethoxy)-5-(2-methoxy-phenoxy)-pyrimidin-4-yl]-benzenesulphonamide, sodium azide and ammonium chloride in DMF there is obtained 4-tert.-butyl-N-[6-(2-hydroxy-ethoxy)-5-(2-methoxy-phenoxy)-2-(4-1H-tetrazol-5-yl-phenyl)-pyrimidin-4-yl]-benzenesulphonamide as a white material.

EXAMPLE 71

In analogy to Example 1, from 4-tert.-butyl-N-[6-chloro-2-(4-cyano-phenyl)-5-(2-methoxy-phenoxy)-pyrimidin-4-yl]-benzenesulphonamide with benzyloxyethanol sodium salt there is obtained N-[6-(2-benzyloxy-ethoxy)-2-(4-cyano-phenyl)-5-(2-methoxy-phenoxy)-pyrimidin-4-yl]-4-tert.-butyl-benzene-sulphonamide of melting point 158–159° C. from EtOAc.

EXAMPLE 72

In analogy to Example 3, from N-[6-(2-benzyloxy-ethoxy)-2-(4-cyano-phenyl)-5-(2-methoxy-phenoxy)-pyrimidin-4-yl]-4-tert.-butyl-benzenesulphonamide, sodium azide and ammonium chloride in DMF there is obtained N-[6-(2-benzyloxy-ethoxy)-5-(2-methoxy-phenoxy)-2-(4-1H-tetrazol-5-yl-phenyl)-pyrimidin-4-yl]-4-tert.-butyl-benzenesulphonamide as a foam.

EXAMPLE 73 a) A solution of 2.1 g (3.4 mmol) of 4-tert.-butyl-N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide in 40 ml of abs. THF is treated with 2 ml of 1-(tert.-butyl-dimethylsilyl)-imidazole and heated to 50° while stirring for one hour. The solution is evaporated under reduced pressure and the residue is recrystallized from methylene chloride and isopropyl ether. There is thus obtained 4-tert.-butyl-N-[6-[2-(tert.-butyl-dimethyl-silanyloxy)-ethoxy]-5-(2-methoxy-phenoxy)-2-(2-1H-tetrazol-5-yl-pyridin-4-yl)-pyrimidin-4-yl]-benzenesulphonamide of melting point 237–239° C. with decomposition.

b) A solution of 366.5 mg (0.5 mmol) of 4-tert.-butyl-N-[6-[2-tert.-butyl-dimethyl-silanyloxy)-ethoxy]-5-(2-methoxy-phenoxy)-2-(2-1H-tetrazol-5-yl-pyridin-4-yl)-pyrimidin-4-yl]-benzenesulphonamide in 30 ml of abs. THF is treated at room temperature with 112.2 mg (1 mmol) of potassium tert.-butylate and the suspension is heated at 40° C. while stirring for 30 min. 1 ml of ethyl bromide is added to the clear solution and the solution is heated at 40° C. for 4 days. Thereafter, the solution is evaporated under reduced pressure, the residue is taken up in a 1:1 mixture of methylene chloride and ether and the organic solution is washed three times with 0.5N NaHCO₃ and thereafter with water. The organic extracts are dried with sodium sulphate and evaporated under reduced pressure. The residue is chromatographed on silica gel with cyclohexane-EtOAc 1:1. Firstly there are isolated 100 mg of 4-tert.-butyl-N-[6-[2-(tert.-butyl-dimethyl-silanyloxy)-ethoxy- 2-[2-(2-ethyl-2H-tetrazol-5-yl)-pyridin-4-yl]-5-(2-methoxy-phenoxy)-pyrimidin-4-yl]-benzenesulphonamide and thereafter 100 mg of 4-tert.-butyl-N-[6-[2-(tert.-butyl-dimethyl-silanyloxy)-2-[2-(1-ethyl-1H-tetrazol-5-yl)-pyridin-4-yl]-5-(2-methoxy-phenoxy)-pyrimidin-4-yl]-benzenesulphonamide.

c) A solution of 90 mg of 4-tert.-butyl-N-[6-[2-(tert.-butyl-dimethyl-silanyloxy)-ethoxy-2-[2-(2-ethyl-2H-tetrazol-5-yl)-pyridin-4-yl]-5-(2-methoxy-phenoxy)-pyrimidin-4-yl]-benzene-sulphonamide in 4 ml of CH₃CN—H₂O 1:1 is treated with 5 drops of trifluoroacetic acid and left at room temperature for 24 hours. Thereafter, acetonitrile is evaporated at 30° C. under reduced pressure and the aqueous phase is treated firstly with 1N NaOH, then with glacial acetic acid to pH 4 and extracted with ether. The organic extracts are washed with H₂O, dried with sodium sulphate and evaporated under reduced pressure. There is thus obtained 4-tert.butyl-N-[2-[2-(2-ethyl-2H-tetrazol-5-yl)-pyridin-4-yl]-6-(2-hydroxy-ethoxy)-5-(2-methoxy-phenoxy)-pyrimidin-4-yl]benzenesulphonamide as a yellowish foam. Analogously, from 4-tert.-butyl-N-[6-[2-(tert.-butyl-dimethyl-silanyloxy)-2-[2-(1-ethyl-1H-tetrazol-5-yl)-pyridin-4-yl]-5-(2-methoxy-phenoxy)-pyrimidin-4-yl]-benzenesulphonamide there is obtained 4-tert.butyl-N-[2-[2-(1-ethyl-1H-tetrazol-5-yl)-pyridin-4-yl]-6-(2-hydroxy-ethoxy)-5-(2-methoxy-phenoxy)-pyrimidin-4-yl]benzenesulphonamide as a yellowish foam.

EXAMPLE A

Tablets containing the following ingredients can be produced in a conventional manner:

| Ingredients | Per tablet |
| --- | --- |
| Compound of formula I | 10.0–100.0 mg |
| Lactose | 125.0 mg |
| Corn starch | 75.0 mg |
| Talc | 4.0 mg |
| Magnesium stearate | 1.0 mg |

EXAMPLE B

Capsules containing the following ingredients can be produced in a conventional manner:

| Ingredients | Per capsule |
| --- | --- |
| Compound of formula I | 25.0 mg |
| Lactose | 150.0 mg |
| Corn starch | 20.0 mg |
| Talc | 5.0 mg |

EXAMPLE C

Injection solutions can have the following composition:

| | |
| --- | --- |
| a) Compound of formula I, e.g. | |
| 4-tert.butyl-N-[6-(2-hydroxy-ethoxy)-5-(2-methoxy-phenoxy)-2-(2-1H-tetrazol-5-yl)-pyridin-4-yl]-pyrimidin-4-yl]-benzenesulphonamide disodium salt | 3.0 mg |
| Gelatine | 150.0 mg |
| Water for injection solutions | ad 1.0 ml |
| b) Compound of formula I, e.g. | |
| 5-methyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide disodium salt | 5.0 mg |
| Gelatine | 150.0 mg |
| Water for injection solutions | ad 1.0 ml |
| c) Compound of formula I, e.g. | |
| 5-isopropyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide disodium salt | 5.0 mg |
| Gelatine | 150.0 mg |
| Water for injection solutions | ad 1.0 ml |

EXAMPLE D 500 mg of compound of formula I are suspended in 3.5 ml of Myglyol 812 and 0.08 g of benzyl alcohol. This suspension is filled into a container having a dosage valve. 5.0 g of Freon 12 are filled into the container under pressure through the valve. The Freon is dissolved in the Myglyol-benzyl alcohol mixture by shaking. This spray container contains about 100 single doses which can be applied individually.

We claim:

1. A compound of the formula:

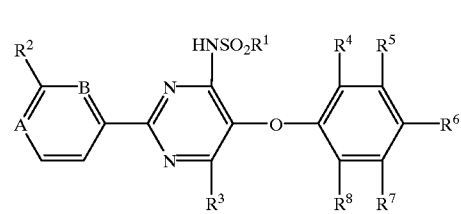

wherein
$R^1$ is phenyl; phenyl substituted with halogen, $C_{1-7}$-alkyl, $C_{1-7}$-alkoxy, $C_{1-7}$-alkylenedioxy, carboxyl, or trifluoromethyl; or heterocyclyl selected from the group consisting of mono- or bicyclic, 5- and 6-membered heterocycles having oxygen, nitrogen or sulphur as the hetero atom;

$R^2$ is tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino, or hydroxyamidino;

$R^3$ is —O—$(CR^aR^b)_n$—$OR^9$;

$R^4$–$R^8$ are each independently hydrogen, $C_{1-7}$-alkoxy, or halogen;

$R^9$ is hydrogen; benzyl; benzyl substituted on the phenyl ring by halogen, $C_{1-7}$-alkyl, $C_{1-7}$-alkoxy, $C_{1-7}$-alkylenedioxy, carboxyl, or trifluoromethyl; or —C(O)$NHR^{10}$;

$R^{10}$ is $C_{1-7}$-alkyl; phenyl; phenyl substituted with halogen, $C_{1-7}$-alkyl, $C_{1-7}$-alkoxy, $C_{1-7}$-alkylenedioxy, carboxyl, or trifluoromethyl; pyridyl; or pyridyl substituted by 1 or 2 $C_{1-7}$-alkyl groups;

R$^a$ and R$^b$ are each hydrogen or C$_{1-7}$-alkyl;

n is 2, 3, or 4;

A and B are each CH; or one of A and B is nitrogen and the other is CH; or a pharmaceutically usable salt thereof.

2. The compound of claim 1, wherein R$^9$ is hydrogen, benzyl, benzyl substituted on the phenyl ring by halogen, C$_{1-7}$-alkyl, C$_{1-7}$-alkoxy, C$_{1-7}$-alkylenedioxy, carboxyl, or trifluoromethyl; or —C(O)NHR$^{10}$.

3. The compound of claim 1, wherein A and B are CH.

4. The compound of claim 1, wherein one of A and B is nitrogen and the other is CH.

5. The compound of claim 4, wherein A is nitrogen and B is CH.

6. The compound of claim 1, wherein R$^2$ is tetrazolyl or C$_1$–C$_7$-alkyl-substituted tetrazolyl.

7. The compound of claim 1, wherein R$^1$ is (i) phenyl that is substituted with one or two substituents selected from the group consisting of halogen, lower-alkyl, C$_1$–C$_7$-alkoxy, C$_1$–C$_7$-alkylenedioxy, carboxyl, and trifluoromethyl, or (ii) pyridyl that is mono-substituted with alkyl; and R$^3$ is —O(CH$_2$)$_n$OH, —O(CH$_2$)$_n$O-benzyl, or —O(CH$_2$)$_n$OC(O)NHR$^{10}$.

8. The compound according to claim 1, wherein R$^4$ is C$_{1-7}$-alkoxy and R$^5$–R$^8$ are hydrogen.

9. The compound according to claim 1, wherein R$^4$ is halogen, R$^7$ is C$_{1-7}$-alkoxy, and R$^5$, R$^6$ and R$^8$ are hydrogen.

10. The compound according to claim 6, wherein the compound of formula I is 5-methyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide.

11. The compound according to claim 6, wherein the compound of formula I is 4-tert-butyl-N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide.

12. The compound according to claim 6, wherein the compound of formula I is 2-[6-(4-tert-butyl-phenylsulphonylamino)-5-(2-methoxy-phenoxy)-2-(2-1H-tetrazol-5-yl-pyridin-4-yl)-pyrimidin-4-yl-oxy]-ethyl pyridin-2-ylcarbamate.

13. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-benzenesulphonamide.

14. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-4-methyl-benzenesulphonamide.

15. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-4-methoxy-benzenesulphonamide.

16. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-4-methylsulphanyl-benzenesulphonamide.

17. The compound according to claim 6, wherein the compound of formula I is 1,3-benzodioxol-5-sulphonic acid 6-(2-hydroxy-ethoxy)-5-(2-methoxy-phenoxy)-2-(2-1H-tetrazol-5-yl-pyridin-4-yl)-pyrimidin-4-ylamide.

18. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-3,4-dimethoxy-benzenesulphonamide.

19. The compound according to claim 6, wherein the compound of formula I is N-[6-(2-hydroxy-ethoxy)-5-(2-methoxy-phenoxy)-2-(2-1H-tetrazol-5-yl-pyridin-4-yl)-pyrimidin-4-yl]-2,5-dimethoxy-benzolsulphonamide.

20. The compound according to claim 6, wherein the compound of formula I is pyridine-3-sulphonic acid 6-(2-hydroxy-ethoxy)-5-(2-methoxy-phenoxy)-2-(2-1H-tetrazol-5-yl-pyridin-4-yl)-pyrimidin-4-ylmide.

21. The compound according to claim 6, wherein the compound of formula I is 4-tert-butyl-N-[5-(2-chloro-5-methoxy-phenoxy)-6-(2-hydroxy-ethoxy)-2-(2-1H-tetrazol-5-yl-pyridin-4-yl)-pyrimidin-4-yl]-benzenesulphonamide.

22. The compound according to claim 6, wherein the compound of formula I is 1,3-benzodioxol-5-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide.

23. The compound according to claim 6, wherein the compound of formula I is 5-isopropyl-pyridin-2-sulphonic acid [5-(2-chloro-5-methoxy-phenoxy)-6-(2-hydroxy-ethoxy)-2-(2-1H-tetrazol-5-yl-pyridin-4-yl)-pyrimidin-4-yl]-amide.

24. The compound according to claim 6, wherein the compound of formula I is 4-tert-butyl-N-[6-(2-hydroxy-ethoxy)-5-(2-methoxy-phenoxy)-2-[6-(1H-tetrazol-5-yl)-pyridin-2-yl]-pyrimidin-4-yl]-benzenesulphonamide.

25. The compound according to claim 6, wherein the compound of formula I is 2-[5-(2-methoxy-phenoxy)-6-phenylsulphonylamino-2-(2-1H-tetrazol-5-yl-pyridin-4-yl)-pyrimidin-4-yloxyl-ethyl pyridin-2-ylcarbamate.

26. The compound according to claim 6, wherein the compound of formula I is 2-[5-(2-methoxy-phenoxy)-6-(4-methyl-phenylsulphonylamino)-2-(2-1H-tetrazol-5-yl-pyridin-4-yl)-pyrimidin-4-yloxy]-ethyl pyridin-2-ylcarbamate.

27. The compound according to claim 6, wherein the compound of formula I is 2-[5-(2-methoxy-phenoxy)-6-(4-methyl-phenylsulphonylamino)-2-(2-1H-tetrazol-5-yl-pyridin-4-yl)-pyrimidin-4-yloxy]-ethyl 1,3-benzodioxol-5-ylcarbamate.

28. The compound according to claim 6, wherein the compound of formula I is 2-[5-(2-methoxy-phenoxy)-6-(4-methylsulphanylphenyl-sulphonylamino)-2-(2-1H-tetrazol-5-yl-pyridin-4-yl)-pyrimidin-4-yloxy]-ethyl pyridin-2-ylcarbamate.

29. The compound according to claim 6, wherein the compound of formula I is 2-[6-(1,3-benzodioxol-5-ylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate.

30. The compound according to claim 6, wherein the compound of formula I is 2-[6-(1,3-benzodioxol-5-ylsulphonylamino)-5-(2-methoxy-phenoxy)-2-(2-1H-tetrazol-5-yl-pyridin-4-yl)-pyrimidin-4-yloxy]-ethyl 1,3-benzodioxol-5-ylcarbamate.

31. The compound according to claim 6, wherein the compound of formula I is 2-[6-(3,4-dimethoxy-phenylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate.

32. The compound according to claim 6, wherein the compound of formula I is 2-[5-(2-methoxy-phenoxy)-6-(2,5-dimethoxy-phenyl-sulphonylamino)-2-(2-1H-tetrazol-5-yl-pyridin-4-yl)-pyrimidin-2-yloxy]-ethyl pyridin-2-ylcarbamate.

33. The compound according to claim 6, wherein the compound of formula I is 2-[5-(2-methoxy-phenoxy)-2-(2-1H-tetrazol-5-yl-pyridin-4-yl)-6-pyridin-3-ylsulphonylamino-pyrimidin-4-yloxy]-ethyl pyridin-2-ylcarbamate.

34. The compound according to claim 6, wherein the compound of formula I is 2-[5-(2-methoxy-phenoxy)-6- pyridin-3-ylsulphonylamino-2-(2-1H-tetrazol-5-yl-pyridin-4-yl)-pyrimidin-4-yloxy]-ethyl 1,3-benzodioxol-5-ylcarbamate.

35. The compound according to claim 6, wherein the compound of formula I is 2-[5-(2-methoxy-phenoxy)-6-(5-methyl-pyridin-2-yl-sulphonylamino)-2-(2-1H-tetrazol-5-yl-pyridin-4-yl)-pyrimidin-4-yloxy]-ethyl pyridin-2-ylcarbamate.

36. The compound according to claim 6, wherein the compound of formula I is 2-[6-(5-isopropyl-pyridin-2-ylsulphonylamino)-5-(2-methoxy-phenoxy)-2-(2-1H-tetrazol-5-yl-pyridin-4-yl)-pyrimidin-4-yloxy]-ethyl pyridin-2-ylcarbamate.

37. The compound according to claim 6, wherein the compound of formula I is 2-[6-(5-isopropyl-pyridin-2-ylsulphonylamino)-5-(2-methoxy-phenoxy)-2-(2-1H-tetrazol-5yl-pyridin-4-yl)-pyrimidin-4-yloxy]-ethyl 1,3-benzodioxol-5-ylcarbamate.

38. The compound according to claim 6, wherein the compound of formula I is 2-[6-(4-tert-butyl-phenylsulphonylamino)-5-(2-chloro-5-methoxy-phenoxy)-2-(2-1H-tertrazol-5-yl-pyridin-4-yl)-pyrimidin-4-yloxy]-ethyl pyridin-2-ylcarbamate.

39. The compound according to claim 6, wherein the compound of formula I is 2-[6-(1,3-benzodioxol-5-ylsulphonylamino)-5-(2-chloro-5-methoxy-phenoxy)-2-(2-1H-tetrazol-5-yl-pyridin-4-yl)-pyrimidin-4-yloxy]-ethyl pyridin-2-ylcarbamate.

40. The compound according to claim 6, wherein the compound of formula I is 2-[6-(4-tert-butyl-phenylsulphonylamino)-5-(2-methoxy-phenoxy)-2-(2-1H-tetrazol-5-yl-pyridin-2-yl)-pyrimidin-4-yloxy]-ethyl pyridin-2-ylcarbamate.

41. The compound according to claim 6, wherein the compound of formula I is N-[6-(2-benzyloxy-ethoxy)-5-(2-methoxy-phenoxy)-2-(2-1H-tetrazol-5-yl-pyridin-4-yl)-pyrimidin-4-yl]-4-tert-butyl-benzenesulphonamide.

42. The compound according to claim 6, wherein the compound of formula I is 4-tert-butyl-N-[2-[2-(1-ethyl-1H-tetrazol-5-yl)-pyridin-4-yl]-6-(2-hydroxy-ethoxy)-5-(2-methoxy-phenoxy)-pyrimidin-4-yl]benzenesulphonamide.

43. The compound according to claim 1, wherein the compound of formula I is 4-tert-butyl-N-[2-(3-cyano-phenyl)-6-(2-hydroxy-ethoxy)-5-(2-methoxy-phenoxy)-pyrimidin-4-yl]-benzenesulphonamide.

44. The compound according to claim 1, wherein the compound of formula I is 4-tert-butyl-N-[6-(2-hydroxy-ethoxy)-5-(2-methoxy-phenoxy)-2-(3-1H-tetrazol-5-yl-phenyl)-pyrimidin-4-yl]-benzenesulphonamide.

45. The compound according to claim 1, wherein the compound of formula I is 2-[6-(4-tert-butyl-phenylsulphonyl)-5-(2-methoxy-phenoxy)-2-(3-1H-tetrazol-5-yl-phenyl)-pyrimidin-4-yloxy]-ethyl pyridin-2-ylcarbamate.

46. The compound according to claim 1, wherein the compound of formula I is N-[6-(2-benzyloxy-ethoxy)-2-(3-cyano-phenyl)-5-(2-methoxy-phenoxy)-pyrimidin-4-yl]-4-tert-butyl-benzenesulphonamide.

47. The compound according to claim 1, wherein the compound of formula I is N-[6-(2-benzyloxy-ethoxy)-5-(2-methoxy-phenoxy)-2-(3-1H-tetrazol-5-yl-phenyl)-pyrimidin-4-yl]- 4-tert-butyl-benzenesulphonamide.

48. The compound according to claim 1, wherein the compound of formula I is 4-tert-butyl-N-[2-(4-cyano-phenyl)-6-(2-hydroxy-ethoxy)-5-(2-methoxy-phenoxy)-pyrimidin-4-yl]-benzenesulphonamide.

49. The compound according to claim 1, wherein the compound of formula I is 4-tert-butyl-N-[6-(2-hydroxy-ethoxy)-5-(2-methoxy-phenoxy)-2-(4-1H-tetrazol-5-yl-phenyl)-pyrimidin-4-yl]-benzenesulphonamide.

50. The compound according to claim 1, wherein the compound of formula I is N-[6-(2-benzyloxy-ethoxy)-2-(4-cyano-phenyl)-5-(2-methoxy-phenoxy)-pyrimidin-4-yl]-4-tert-butyl-benzenesulphonamide.

51. The compound according to claim 1, wherein the compound of formula I is N-[6-(2-benzyloxy-ethoxy)-5-(2-methoxy-phenoxy)-2-(4-1H-tetrazol-5-yl-phenyl)-pyrimidin-4-yl]-4-tert-butyl-benzenesulphonamide.

52. The compound according to claim 4, wherein the compound of formula I is 4-tert-butyl-N-[2-(2-cyano-pyridin-4-yl)-6-(2-hydroxy-ethoxy)-5-(2-methoxy-phenoxy)-pyrimidin-4-yl]-benzenesulphonamide.

53. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-benzenesulphonamide.

54. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-4-methyl benzenesulphonamide.

55. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-4-methoxy-benzenesulphonamide.

56. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-4-methylsulphanyl-benzenesulphonamide.

57. The compound according to claim 4, wherein the compound of formula I is 1,3-benzodioxol-5-sulphonic acid 2-(2-cyano-pyridin-4-yl)-6-(2-hydroxy-ethoxy)-5-(2-methoxy-phenoxy)-pyrimidin-4-ylamide.

58. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-3,4-dimethoxy-benzene-sulphonamide.

59. The compound according to claim 4, wherein the compound of formula I is N-[2-(2-cyano-pyridin-4-yl)-6-(2-hydroxy-ethoxy)-5-(2-methoxy-phenoxy)-pyrimidin-4-yl]-2,5-dimethoxy-benzene-sulphonamide.

60. The compound according to claim 4, wherein the compound of formula I is pyridine-3-sulphonic acid 2-(2-cyano-pyridin-4-yl)-6-(2-hydroxy-ethoxy)-5-(2-methoxy-phenoxy)-pyrimidin-4-ylamide.

61. The compound according to claim 4, wherein the compound of formula I is 5-methyl-pyridine-2-sulphonic acid 2-(2-cyano-pyridin-4-yl)-6-(2-hydroxy-ethoxy)-5-(2-methoxy-phenoxy)-pyrimidin-4-ylamide.

62. The compound according to claim 4, wherein the compound of formula I is 5-isopropyl-pyridine-2-sulphonic acid 2-(2-cyano-pyridin-4-yl)-6-(2-hydroxy-ethoxy)-5-(2-methoxy-phenoxy)-pyrimidin-4-ylamide.

63. The compound according to claim 4, wherein the compound of formula I is 4-tert-butyl-N-[5-(2-chloro-5-methoxy-phenoxy)-2-(2-cyano-pyridin-4-yl)-6-(2-hydroxy-ethoxy)-pyrimidin-4-yl]-benzenesulphonamide.

64. The compound according to claim 4, wherein the compound of formula I is 1,3-benzodioxol-5-sulphonic acid 5-(2-chloro-5-methoxy-phenoxy)-2-(2-cyano-pyridin-4-yl)-6-(2-hydroxy-ethoxy)-pyrimidin-4-ylamide.

65. The compound according to claim 4, wherein the compound of formula I is 5-isopropyl-pyridine-2-sulphonic acid 5-(2-chloro-5-methoxy-phenoxy)-2-(2-cyano-pyridin-4-yl)-6-(2-hydroxy-ethoxy)-pyrimidin-4-ylamide.

66. The compound according to claim 4, wherein the compound of formula I is 4-tert-butyl-N-[2-(6-cyanopyridin-2-yl)-6-(2-hydroxy-ethoxy)-5-(2-methoxy-phenoxy)-pyrimidin-4-yl]-benzenesulphonamide.

67. The compound according to claim 4, wherein the compound of formula I is N-[6-(2-benzyloxy-ethoxy)-2-(2-cyano-pyridin-4-yl)-5-(2-methoxy-phenoxy)-pyrimidin-4-yl]-4-tert-butyl-benzenesulphon-amide.

68. The compound according to claim 4, wherein the compound of formula I is 5-isopropyl-pyridine-2-sulphonic acid-N-[6-(2-benzyloxy-ethoxy)-2-(2-cyanopyridin-4-yl)-5-(2-methoxyphenoxy)-pyrimidin-4-yl]-amide.

69. The compound according to claim 4, wherein the compound of formula I is 4-tert-butyl-N-[2-[2-(amino-imino-methyl)-pyridin-4-yl]-6-(2-hydroxy-ethoxy)-5-(2-methoxy-phenoxy)-pyrimidin-4-yl]-benzenesulphonamide.

70. The compound according to claim 3, wherein the compound of formula I is ethyl 4-[4-tert-butyl-phenylsulphonylamino)-6-(2-hydroxy-ethoxy)-5-(2-methoxy-phenoxy)-pyrimidin-2-yl]-pyridine-2-carboxylate.

71. The compound according to claim 3, wherein the compound of formula I is 4-[4-(4-tert-butyl-phenylsulphonylamino)-6-(2-hydroxy-ethoxy)-5-(2-methoxy-phenoxy)-pyrimidin-2-yl]-pyridine-2-carboxylic acid.

72. The compound according to claim 6, wherein the compound of formula I is 2-[5-(2-methoxy-phenoxy)-6-(4-methyl-phenylsulphonyl-amino)-2-(2-1H-tetrazol-5-yl-pyridin-2-yl)-pyrimidin-4-yloxy]-ethyl pyridin-2-ylcarbamate.

73. The compound according to claim 6, wherein the compound of formula I is 2-[5-(2-methoxy-phenoxy)-6-(4-methoxy-phenylsulphonyl-amino)-2-(2-1H-tetrazol-5-yl-pyridin-4-yl)-pyrimidin-4-yloxy]-ethyl 1,3-benzodioxol-5-ylcarbamate.

74. The compound according to claim 6, wherein the compound of formula I is 2-[5-(2-chloro-5-methoxy-phenoxy)-6-(5-isopropyl-pyridin-2-ylsulphonylamino)]-2-(2-1H-tertrazol-5-yl-pyridin-2-yl)-pyrimidin-4-yloxy]-ethyl pyridin-2-ylcarbamate.

75. The compound according to claim 6, wherein the compound of formula I is 5-methyl-pyridine-2-sulphonic acid [6-(2-benzyloxy-ethoxy)-5-(2-methoxy-phenoxy)-2-(2-1H-tertrazol-5-yl-pyridin-4-yl) ]-amide.

76. The compound according to claim 6, wherein the compound of formula I is 5-isopropyl-pyridine-2-sulphonic acid [6-(2-benzyloxy-ethoxy)-5-(2-methoxy-phenoxy)-2-[2-(1H-tetrazol-5-yl)-pyridin-4-yl]-pyrimidin-4-yl]-amide.

77. The compound according to claim 6, wherein the compound of formula I is 4-tert-butyl-N-[2-[2-(hydroxyamino-imino-methyl)-pyridin-4-yl]-6-(2-hydroxy-ethoxy)-5-(2-methoxy-phenoxy)-pyrimidin-4-yl]-benzenesulphonamide.

78. The compound according to claim 6, wherein the compound of formula I is 5-isopropyl-pyridine-2-sulphonic acid 6-(2-hydroxy-ethoxy)-5-(2-methoxy-phenoxy)-2-(2-1H-tetrazol-5-yl-pyridin-4-yl)-pyrimidin-4-ylamide.

79. A step in a process for making a compound of the formula:

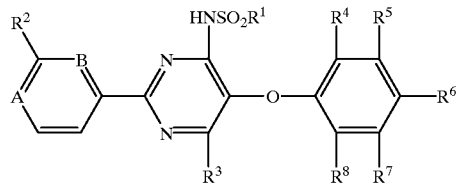

wherein
$R^1$ is phenyl; phenyl substituted with halogen, $C_{1-7}$-alkyl, $C_{1-7}$-alkoxy, $C_{1-7}$-alkylenedioxy, carboxyl, or trifluoromethyl; or heterocyclyl selected from the group consisting of mono- or bicyclic, 5- and 6-membered heterocycles having oxygen, nitrogen or sulphur as the hetero atom;
$R^2$ is tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino, or hydroxyamidino;
$R^3$ is —O—$(CR^aR^b)_n$—$OR^9$;
$R^4$–$R^8$ are each independently hydrogen, $C_{1-7}$-alkoxy, or halogen;
$R^9$ is hydrogen; benzyl; benzyl substituted on the phenyl ring by halogen, $C_{1-7}$-alkyl, $C_{1-7}$-alkoxy, $C_{1-7}$-alkylenedioxy, carboxyl, or trifluoromethyl; or —C(O) $NHR^{10}$;
$R^{10}$ is $C_{1-7}$-alkyl; phenyl; phenyl substituted with halogen, $C_{1-7}$-alkyl, $C_{1-7}$-alkoxy, $C_{1-7}$-alkylenedioxy, carboxyl, or trifluoromethyl; pyridyl; or pyridyl substituted by 1 or 2 $C_{1-7}$-alkyl groups;
$R^a$ and $R^b$ are each hydrogen or $C_{1-7}$-alkyl;
n is 2, 3, or 4;
A and B are each CH; or one of A and B is nitrogen and the other is CH;
which comprises:
reacting a compound of the formula:

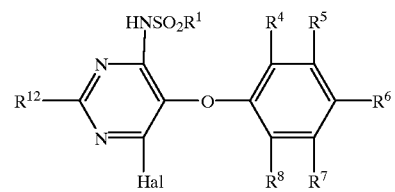

wherein
$R^{12}$ is 3-cyanophenyl, 4-cyanophenyl, 2-pyridyl-N-oxide, or 4-pyridyl-N-oxide;
Hal is halogen; and
$R^1$, $R^4$, $R^5$, $R^6$, $R^7$, and $R^8$ are as above;
with a compound of the formula MO—$(CR^aR^b)_n$—$OR^{91}$, wherein
M is an alkali metal;
$R^{91}$ is hydrogen; benzyl; benzyl substituted on the phenyl ring by halogen, $C_{1-7}$-alkyl, $C_{1-7}$-alkoxy, $C_{1-7}$-alkylenedioxy, carboxyl, or trifluoromethyl; and
$R^a$, $R^b$, and n are as above.

80. A step in a process for making a compound of the formula:

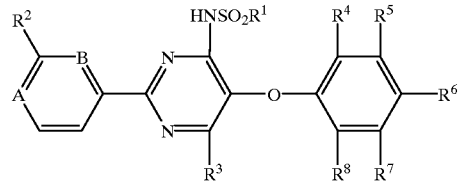

wherein
$R^1$ is phenyl; phenyl substituted with halogen, $C_{1-7}$-alkyl, $C_{1-7}$-alkoxy, $C_{1-7}$-alkylenedioxy, carboxyl, or trifluoromethyl; or heterocyclyl selected from the group consisting of mono- or bicyclic, 5- and 6-membered heterocycles having oxygen, nitrogen or sulphur as the hetero atom;
$R^2$ is tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino, or hydroxyamidino;

$R^3$ is —O—$(CR^aR^b)_n$—$OR^9$;

$R^4$–$R^8$ are each independently hydrogen, $C_{1-7}$-alkoxy, or halogen;

$R^9$ is hydrogen; benzyl; benzyl substituted on the phenyl ring by halogen, $C_{1-7}$-alkyl, $C_{1-7}$-alkoxy, $C_{1-7}$-alkylenedioxy, carboxyl, or trifuoromethyl; or —C(O)NHR$^{10}$;

$R^{10}$ is $C_{1-7}$-alkyl; phenyl; phenyl substituted with halogen, $C_{1-7}$-alkyl, $C_{1-7}$-alkoxy, $C_{1-7}$-alkylenedioxy, carboxyl, or trifluoromethyl; pyridyl; or pyridyl substituted by 1 or 2 $C_{1-7}$-alkyl groups;

$R^a$ and $R^b$ are each hydrogen or $C_{1-7}$-alkyl;

n is 2, 3, or 4;

A and B are each CH; or one of A and B is nitrogen and the other is CH; or $R^2$ is hydrogen and one of A and B is N-oxide and the other is CH;

which comprises:

reacting a compound of the formula:

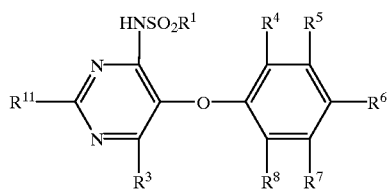

III wherein $R^{11}$ is 2-pyridyl-N-oxide, or 4-pyridyl-N-oxide; and $R^1$, $R^3$, $R^4$, $R^5$, $R^6$, $R^7$, and $R^8$ are as above;

with a trialkylsilyl cyanide and a trialkylamine.

81. A pharmaceutical composition which comprises:

(a) from 3 mg to 100 mg of a compound of the formula:

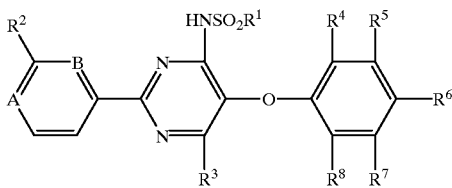

I wherein $R^1$ is phenyl; phenyl substituted with halogen, $C_{1-7}$-alkyl, $C_{1-7}$-alkoxy, $C_{1-7}$-alkylenedioxy, carboxyl, or trifluoromethyl; or heterocyclyl selected from the group consisting of mono- or bicyclic, 5- and 6-membered heterocycles having oxygen, nitrogen or sulphur as the hetero atom;

$R^2$ is tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino, or hydroxyamidino;

$R^3$ is —O—$(CR^aR^b)_n$—$OR^9$;

$R^4$–$R^8$ are each independently hydrogen, $C_{1-7}$-alkoxy, or halogen;

$R^9$ is hydrogen; benzyl; benzyl substituted on the phenyl ring by halogen, $C_{1-7}$-alkyl, $C_{1-7}$-alkoxy, $C_{1-7}$-alkylenedioxy, carboxyl, or trifuoromethyl; or —C(O)NHR$^{10}$;

$R^{10}$ is $C_{1-7}$-alkyl; phenyl; phenyl substituted with halogen, $C_{1-7}$-alkyl, $C_{1-7}$-alkoxy, $C_{1-7}$-alkylenedioxy, carboxyl, or trifluoromethyl; pyridyl; or pyridyl substituted by 1 or 2 $C_{1-7}$-alkyl groups;

$R^a$ and $R^b$ are each hydrogen or $C_{1-7}$-alkyl;

n is 2, 3, or 4;

A and B are each CH; or one of A and B is nitrogen and the other is CH; or a pharmaceutically usable salt thereof; and (b) a therapeutically inert carrier.

82. The pharmaceutical composition of claim 81, wherein the composition comprises 3 mg of a compound of formula I.

83. The pharmaceutical composition of claim 81, wherein the composition comprises 5 mg of the compound of formula I.

84. The pharmaceutical composition of claim 81, wherein the composition comprises from 10 mg to 100 mg of the compound of formula I.

85. The pharmaceutical composition of claim 84, wherein the composition comprises from 25 mg of the compound of formula I.

86. A method of treating circulatory disorders, which comprises administering to a host in need of such treatment an effective amount of the compound of the formula:

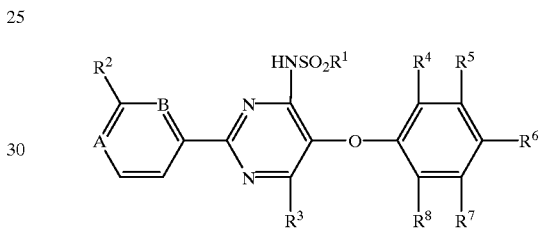

I wherein $R^1$ is phenyl; phenyl substituted with halogen, $C_{1-7}$-alkyl, $C_{1-7}$-alkoxy, $C_{1-7}$-alkylenedioxy, carboxyl, or trifluoromethyl; or heterocyclyl selected from the group consisting of mono- or bicyclic, 5- and 6-membered heterocycles having oxygen, nitrogen or sulphur as the hetero atom;

$R^2$ is tetrazolyl, $C_{1-7}$-alkyl-substituted tetrazolyl, cyano, carboxy, $C_{1-7}$-alkoxycarbonyl, hydroxymethyl, formyl, carbamoyl, thiocarbamoyl, amidino, or hydroxyamidino;

$R^3$ is —O—$(CR^aR^b)_n$—$OR^9$;

$R^4$–$R^8$ are each independently hydrogen, $C_{1-7}$-alkoxy, or halogen;

$R^9$ is hydrogen; benzyl; benzyl substituted on the phenyl ring by halogen, $C_{1-7}$alkyl, $C_{1-7}$-alkoxy, $C_{1-7}$-alkylenedioxy, carboxyl, or trifluoromethyl; or —C(O)NHR$^{10}$;

$R^{10}$ is $C_{1-7}$-alkyl; phenyl; phenyl substituted with halogen, $C_{1-7}$-alkyl, $C_{1-7}$-alkoxy, $C_{1-7}$-alkylenedioxy, carboxyl, or trifluoromethyl; pyridyl; or pyridyl substituted by 1 or 2 $C_{1-7}$-alkyl groups;

$R^a$ and $R^b$ are each hydrogen or $C_{1-7}$-alkyl;

n is 2, 3, or 4;

A and B are each CH; or one of A and B is nitrogen and the other is CH; or a pharmaceutically usable salt thereof.

* * * * *

UNITED STATES PATENT AND TRADEMARK OFFICE
CERTIFICATE OF CORRECTION

PATENT NO. : 6,004,965
DATED : December 21, 1999
INVENTOR(S) : Volker Breu et al.

It is certified that error appears in the above-identified patent and that said Letters Patent is hereby corrected as shown below:

Column 24, claim 25, line 25, "pyrimidin-4-yloxyl-ethyl" should be
-- pyrimidin-4-yloxy]-ethyl --

Signed and Sealed this

Twelfth Day of September, 2000

Attest:

Q. TODD DICKINSON

*Attesting Officer*    *Director of Patents and Trademarks*